United States Patent [19]
Compans et al.

[11] Patent Number: 6,077,662
[45] Date of Patent: Jun. 20, 2000

[54] VIRUS-LIKE PARTICLES, METHODS AND IMMUNOGENIC COMPOSITIONS

[75] Inventors: Richard W. Compans, Atlanta, Ga.; Galina V. Yamshchikov, Charlottesville, Va.

[73] Assignee: Emory University, Atlanta, Ga.

[21] Appl. No.: 08/980,050

[22] Filed: Nov. 26, 1997

Related U.S. Application Data

[60] Provisional application No. 60/031,972, Nov. 27, 1996.

[51] Int. Cl.$^7$ .......................... C12P 21/06; A61K 39/21; C07H 21/04; C12Q 1/70
[52] U.S. Cl. .......................... 435/5; 424/208.1; 435/348; 435/69.1; 435/69.3; 536/23.72; 536/24.1
[58] Field of Search ................... 435/69.1, 348, 435/5, 69.3; 536/23.72, 24.1; 424/208.1

[56] References Cited

U.S. PATENT DOCUMENTS

| | | | |
|---|---|---|---|
| 5,462,734 | 10/1995 | Letchworth, III et al. | 424/229.1 |
| 5,541,062 | 7/1996 | Smeekens et al. | 435/6 |
| 5,561,228 | 10/1996 | Or et al. | 540/456 |
| 5,562,909 | 10/1996 | Allcock et al. | 424/280.1 |
| 5,562,910 | 10/1996 | Daynes et al. | 424/278.1 |
| 5,571,531 | 11/1996 | McDermott et al. | 424/459 |

FOREIGN PATENT DOCUMENTS

| | | | |
|---|---|---|---|
| 89/06279 | 7/1989 | WIPO | C12N 9/50 |
| 92/22654 | 12/1992 | WIPO | C12N 15/49 |

OTHER PUBLICATIONS

Yamshchikov, G.V., et al. "Assembly of SIV virus–like particles containing envelope proteins using a baculovirus expression system", (1995), *Virol.* 214:50–58.

Vzorov, A.N., and Compans, R.W. "Assembly and release of SIV Env proteins with full–lenght or truncated cytoplasmic domains", (1996), *Virol.* 221:22–33.

Luo, L., et al. "Expression of gag precursor protein and secretion of virus–like gag particles of HIV–2 from recombinant baculovirus–infected insect cells", (1990), *Virol.* 179:874–880.

Porter, D.C., et al. "Release of virus–like particles from cells infected with poliovirus replicons which express human immunodeficiency virus type 1 gag", (1996), *J. of Virol.* 70(4):2643–2649.

Morikawa, S., et al. "Analyses of the requirements for the synthesis of virus–like particles by feline immunodeficiency virus gag using baculovirus vectors", (1991), *Virol.* 183:288–297.

Zingler, K. and Littman, D.R. "Truncation of the cytoplasmic domain of the simian immunodeficiency virus envelope glycoprotein increases Env incorporation into particles and fusogenicity and infectivity", (1993), *J. of Virol.* 67(3):2824–2831.

Haffar, O.K., et al. "Inhibition of virus production in peripheral blood mononuclear cells from human immunodeficiency virus (HIV) type 1–seropositive donors by treatment with recombinant HIV–like particles", (1992), *J. of Virol.* 66(7):4279–4287.

(List continued on next page.)

*Primary Examiner*—Jeffrey Stucker
*Assistant Examiner*—Hankyel T. Park
*Attorney, Agent, or Firm*—Greenlee, Winner and Sullivan, PC

[57] ABSTRACT

The present disclosure provides retrovirus-like particles which comprise retrovirus env proteins, immunogenic compositions comprising retrovirus-like particles, methods for the production of retrovirus-like particles and methods for the protection of an animal or a human from retrovirus infection using the retrovirus-like particles of the present invention.

24 Claims, 6 Drawing Sheets

OTHER PUBLICATIONS

Rovinski, B., et al. "Expression and characterization of genetically engineered human immunodeficiency virus–like particles containing modified envelope glycoproteins: Implications for development of a cross–protective AIDS vaccine", (1992), *J. of Virol.* 66(7):4003–4012.

Kräusslich, H–G., et al. "Analysis of protein expression and virus–like particle formation in mammalian cell lines stably expressing HIV–1 gag and env gene products with or without active HIV proteinase", (1993), *Virol.* 192:605–617.

Vzorov, A.N., et al. "Highly immunogenic human immunodeficiency viruslike particles are produced by recombinant vaccinia virus–infected cells", (1991), *AIDS Res. Hum. Retr.* 7(1):29–36.

Haffar, O., et al. "Human immunodeficiency virus–like, nonreplicating, gag–env particles assemble in a recombinant vaccinia virus expression system", (1990), *J. of Virol.* 64(6):2653–2659.

Haffar, O.K., et al. "HIV–specific humoral and cellular immunity in rabbits vaccinated with recombinant human immunodeficiency virus–like–gag–env particles", (1991), *Virol.* 183:487–495.

Delchambre, M., et al. "The GAG precursor of simian immunodeficiency virus assembles into virus–like particles", (1989), *EMBO J.* 8(9):2653–2660.

Wills, J.W. and Craven R.C. "Form, function, and use of retroviral Gag proteins", (1991), *AIDS* 5:639–654.

Vincent, M.J., et al. "Characterization of a novel baboon virus closely resembling human t–cell leukemia virus", (1996), *Virol.* 226:57–65.

Haynes, J.R., et al. "Production of immunogenic HIV–1 viruslike particles in stably engineered monkey cell lines", (1991), *AIDS Res. Hum. Retr.* 7(1):17–27.

Dong, J. and Hunter, E. "Analysis of retroviral assembly using a vaccinia/T7–polymerase complementation system", (1993), *Virol.* 194:192–199.

Ball, J.M. et al. "EIAV genomic organization: further characterization by sequencing of purified glycoproteins and cDNA," (1988), *Virology,* 165:601–605.

Chazal, N. et al. "Human immunodeficiency virus type 1 MA deletion mutants expressed in baculovirus–infected cells: cis and trans effects on the Gag precursor assembly pathway," (1995), *J. Virol.,* 69:365–375.

Boomer, S. et al. "Isolation of a novel subgroup B feline leukemia virus from a cat infected with FeLV–A," (1994), *Virology,* 204:805–810.

Zhou, W., et al. "Identification of membrane–binding domain within the amino–terminal region of human immunodeficiency virus type 1 gag protein which interacts with acidic phospholipids", (1994), *J. Virol.* 68:2556–2569.

Yuan, X. et al. "Mutations in the N–terminal region of human immunodeficiency virus type 1 matrix protein block intracellular transport of the Gag precursor," (1993), *J. Virol.,* 67:6387–6394.

Yu, X., et al. "The matrix protein of human immunodeficiency virus type 1 is required for incorporation of viral envelope protein into mature virus", (1992), *J. Virol.* 66:4966–4971.

Willey, R.L. et al. "Biosynthesis, cleavage, and degradation of the human immunodeficiency virus 1 envelope glycoprotein gp160," (1988), *Proc. Natl. Acad. Sci. USA,* 85:9580–9584.

Wang, B. et al. "Molecular cloning, expression, and biological characterization of an HTLV–II envelope glycoprotein: HIV–1 expression is permissive for HTLV–II induced cell fusion," (1993), *AIDS Res. Hum. Retroviruses,* 9:849–860.

Vile, R.G., et al. "A murine cell line producing HTLV–I pseudotype virions carrying a selectable marker gene", (1991), *Virol.* 180:420–424.

Vey, M. et al. "Maturation of the trans–Golgi network protease furin: compartmentalization of propeptide removal, substrate cleavage, and COOH–terminal truncation," (1994), *J. Cell Biol.,* 127:1829–1842.

Spies, C.P., et al. "Truncation of the cytoplasmic domain of the simian immunodeficiency virus envelope glycoprotein alters conformation of the external domain", (1994), *J. Virol.* 68:585–591.

Schlitz, R., et al. "Equine infectious anemia virus gene expression: characterization of the RNA splicing pattern and the protein products encoded by open reading frames S1 and S2," (1992), *J. Virol.,* 66:3455–3465.

Rushlow, K. et al. "Lentivirus genomic organization: the complete nucleotide sequence of the env gene region of equine infectious anemia virus," (1986), *Virology,* 155:309–321.

Royer, M. et al. "Functional domains of HIV–1 Gag polyprotein expressed in baculovirus–infected cells," (1991), *Virology,* 184:417–422.

Rohn, J.L., et al. "Evolution of feline leukemia virus variant genomes with insertions, deletions, and defective envelope genes in infected cats with tumors", (1994), *J. Virol.* 68:2458–2467.

Ritter, D.G., et al. "Cell fusion activity of the simian immunodeficiency virus envelope protein is modulated by the intracytoplasmic domain," (1993), *Virology,* 197:255–264.

Pique, C. et al. "Mutations introduced along the HTLV–I envelope gene result in a non–functional protein: a basis for envelope conservation?" (1990), *EMBO J.,* 9:4243–4248.

Pancino, G., et al. "Differences in feline immunodeficiency virus host cell range correlate with envelope fusogenic properties," (1995), *Virology,* 206:796–806.

Page, K.A. et al. "Analysis of mutations in the V3 domain of gp160 that affedct fusion and infectivity," (1992), *J. Virol.,* 66:524–533.

Overton, H.A., et al. "The protease and gag gene products of the human immunodeficiency virus: authentic cleavage and post–translational modification in an insect cell expression system", (1989), *Virol.* 170:107–116.

Morikawa, Y. et al. "Legitimate and illegitimate cleavage of human immunodeficiency virus glycoproteins by furin," (1993), *J. Virol.,* 67:3601–3604.

Mulligan, M.J., et al. "Cytoplasmic domain truncation enhances fusion activity by the exterior glycoprotein complex of human immunodeficiency virus type 2 in selected cell types", (1992), *J. Virol.* 66:3971–3975.

Moore, J., et al. "Which gp160 vaccine?", (1993), *Nature* 361:503.

Moldoveanu, Z., et al. "Immune Responses to influenza virus in orally and systemically immunized mice", (1989), *Curr. Top. Microbiol. Immunol.* 146:91–99.

McCune, J.M., et al. "Endoproteolytic cleavage of gp160 is required for the activation of human immunodeficiency virus," (1988), *Cell,* 53:55–67.

Marx, P.A., et al. "Protection against SIV vaginal transmission with microencapsulated vaccine", (1993), *Science* 260:1323–1327.

Lehner, T., et al. "Induction of mucosal and systemic immunity to a recombinant simian immunodeficiency viral protein", (1992), *Science* 258:1365–1369.

Lee, P.P. and Linial, M.L. "Efficient particle formation can occur if the matrix domain of human immunodeficiency virus type 1 gag is substituted by a myristilation signal", (1994), *J. Virol.* 68:6644–6654.

Julius, et al. "Isolation of the putative structural gene for the lysine–arginine–cleaving endopeptidase required for processing of yeast pre–pro–alpha factor," (1984), *Cell,* 37:1075–1089.

Jenkins, S., et al. "Formation of lentivirus particles by mammalian cells infected with recombinant fowlpox virus", (1991), *AIDS Res. Hum. Retr.* 7:991–998.

Hughes, B.P., et al. "Morphogenic capabilities of human immunodeficiency virus type 1 gag and gag–pol proteins in insect cells", (1993), *Virol.* 193:242–255.

Hu, S–L., et al. "Expression of envelope glycoproteins of human immunodeficiency virus by an insect virus vector", (1987), *J. Virol.* 176:3617–3620.

Hallenberger, S., et al. "Inhibition of furin–mediated cleavage activation of HIV–1 glycoprotein gp160", (1992), *Nature* 360:358–361.

Haigwood, N.L., et al. "Native but not denatured recombinant human immunodeficiency virus type 1 gp120 generates broad–spectrum neutralizing antibodies in baboons", (1992), *J. Virol.* 66:172–182.

Guo, H–G., et al. "Characterization of an HIV–1 point mutant blocked in envelope glycoprotein cleavage", (1990), *Virol.* 174:217–224.

Ghosh, S.K., et al. "A molecular clone of HIV–1 tropic and cytopathic for human and chimpanzee lymphocytes", (1993), *Virol.* 194:858–864.

Gabuzda, D.H., et al. "Effects of deletions in the cytoplasmic domain on biological functions of human immunodeficiency virus type 1 envelope glycoproteins", (1992), *J. of Virol.* 66:3306–3315.

Eldridge, J.H., et al. "Vaccine delivery system for oral immunization", (1989), *Curr. Top. Microbiol. Immunol.* 146:59–66.

Dorfman, T., et al. "Role of the matrix protein in the virion association of the human immunodeficiency virus type 1 envelope glycoprotein", (1994), *J. Virol.* 68:1689–1696.

Dertzbaugh, M.T. and Elson, C.O. "Comparative effectiveness of the cholera toxin B subunit and alkaline phosphatase as carriers for oral vaccines", (1989), *Infect. Immun.* 61:48–55.

Cunningham, T.P., et al. "Lentivirus envelope sequences and proviral genomes are stabilized in *Escherichia coli* when cloned in low–copy–number plasmid vectors.", (1993), *Gene* 124:93–98.

FIG. 2A
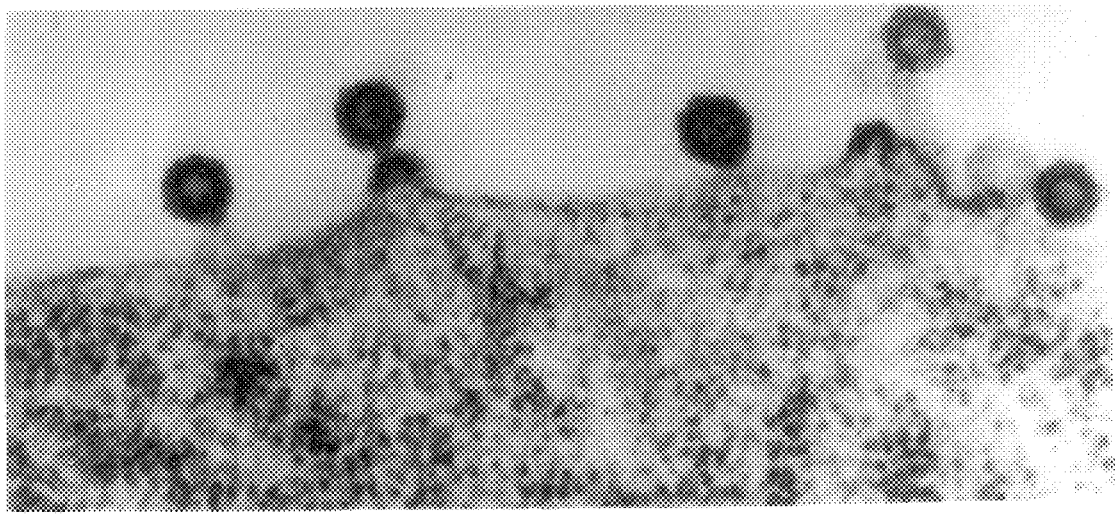
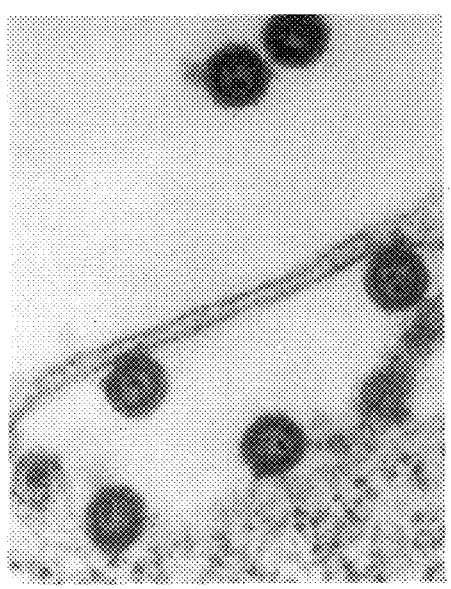
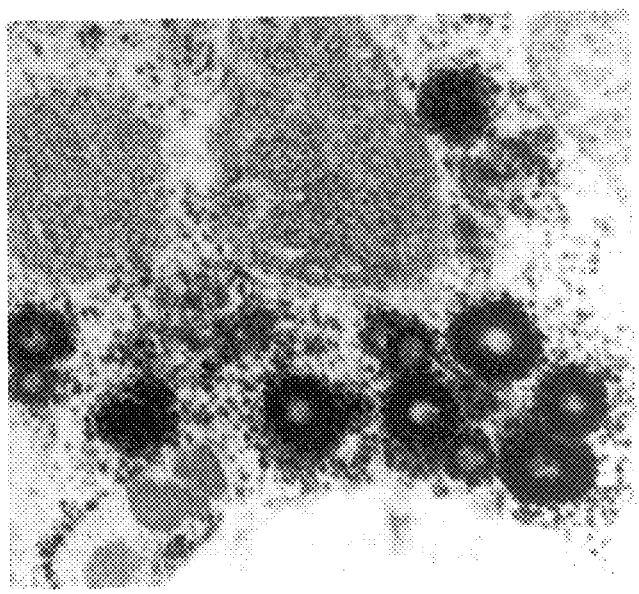
FIG. 2B
FIG. 2C

VIRUS-LIKE PARTICLES, METHODS AND IMMUNOGENIC COMPOSITIONS

CROSS-REFERENCE TO RELATED APPLICATION

This application claims priority from U.S. Provisional Patent Application Ser. No. 60/031,972, filed Nov. 27, 1996, which is incorporated by reference herein in its entirety.

ACKNOWLEDGEMENT OF FEDERAL RESEARCH FUNDING

This invention was made, at least in part, with funding from the National Institutes of Health (Grant Nos. AI 28147, AI 34242 and AI 35821). Accordingly, the United States Government has certain rights in this invention.

BACKGROUND OF THE INVENTION

The field of the present invention is retroviruses and nucleic acid-free particles, methods of producing immunogenic retrovirus-like particles using baculovirus vectors, immunogenic compositions comprising retrovirus-like particles and methods for eliciting an immune response using compositions comprising retrovirus-like particles.

Assembly of virus particles of the lentivirus genus of retroviruses takes place by a budding process at the cellular plasma membrane. Representative lentiviruses include Simian Immunodeficiency Virus (SIV) and Human Immunodeficiency Virus (HIV). Studies with several retroviruses have demonstrated that the Gag protein expressed in the absence of other viral components is self-sufficient for particle formation and budding at the cell surface (Wills and Craven, 1991). Immature virus particles undergo a process of maturation wherein the viral protease cleaves the Gag precursor into the structural proteins: matrix, core and nucleocapsid proteins (Wills and Craven, 1991). It has been reported that the N-terminal region of the Gag precursor is a targeting signal for transport to the cell surface and membrane binding, which is required for virus assembly (Yuan et al., 1993; Zhou et al., 1994). The mechanism of specific incorporation of envelope protein in the virus particles is not understood, but interaction of Env with matrix protein p17 seems to be important (Yu et al., 1992; Dorfman et al., 1994).

Assembly of recombinant HIV-like particles that contain Gag structural proteins as well as Env glycoproteins gp120 and gp41 was previously reported using a vaccinia virus expression system (Haffar et al., 1990; Vzorov et al., 1991). These particles reportedly induce HIV-specific humoral and cellular immunity in rabbits (Haffar et al., 1991) and can inhibit virus production in latently infected peripheral blood mononuclear cells from HIV-1 seropositive donors (Haffar et al., 1992). Formation of retrovirus-like immature particles upon expression of the Gag precursor in insect cells using baculovirus vectors was demonstrated by several groups (Delchambre et al., 1989; Luo et al., 1990; Royer et al., 1991; Morikawa et al., 1991). These Gag particles resemble immature lentivirus particles which are efficiently assembled and released by budding from the insect cell membrane. In contrast to the expression in mammalian cells, inclusion of the protease region in Gag expressing vectors in the baculovirus system leads to overexpression of the protease and early processing of the Gag precursor into mature structural proteins within insect cells, which prevents particle formation (Morikawa et al., 1991; Hughes et al., 1993).

The expression patterns of retroviral envelope glycoproteins in the baculovirus system have several disadvantages in comparison to expression in mammalian cells. The proteins are cleaved very inefficiently and are mainly cell associated (Rusche et al., 1987; Wells and Compans, 1990; Hu et al., 1987). However, HIV-1 Env proteins produced in insect cells are immunologically and biologically active, as demonstrated by their ability to react specifically with immune serum (Hu et al., 1987) and to induce syncytium formation upon co-cultivation with HeLa T4 cells (Wells and Compans, 1990). Because of conditions used for purification of Env glycoproteins from baculovirus-infected insect cells, the preparations obtained often contain denatured gp160, which has little immunogenic activity (Moore et al., 1993). Nevertheless in some cases, as reported by Rusche et al. (1987), immunization with a crude lysate of HIV-1 Env expressing insect cells produced high titers of virus neutralizing and fusion blocking antibody in experimental animals.

The assembly of envelope proteins into HIV, SIV or other retrovirus-like particles has not been reported previously using baculovirus expression systems, possibly because of limitations in the transport and surface expression of the envelope glycoproteins.

SUMMARY OF THE INVENTION

It is an object of the present invention to provide retrovirus-like particles which comprise envelope proteins or truncated envelope proteins embedded within the membranes thereof. Specifically exemplified retrovirus-like particles, also termed virus-like particles (VLPs) herein, of the present invention include those of SIV and HIV. Within the scope of the present invention are retrovirus-like particles prepared using the methods disclosed hereinbelow using envelope proteins from bovine immunodeficiency virus, bovine leukemia virus, feline leukemia virus, feline immunodeficiency virus (FIV), equine infectious anemia virus and human T cell leukemia virus type I, among others. Preferably the VLPs further comprise viral structural proteins derived from a recombinantly expressed precursor Gag protein coding sequence. It is further preferred that the VLPs comprise a truncated envelope protein, wherein the truncation improves expression and assembly of VLPs without deleting antigenic determinants important in protective immunity when the VLPs are administered in immunogenic compositions.

The present invention provides an improved method for the production of retrovirus-like particles, wherein the virus envelope coding sequence (or a truncation thereof) is inserted in a baculovirus vector and expressed under the regulatory control of a promoter such as a late or a late/very late hybrid promoter, and co-expressed in an insect cell in which the protein-processing protease, such as the furin protease, is also expressed. The furin (or other mammalian protease in the KEX protease family) improves the processing efficiency of the cells in which the baculovirus-envelope sequence is expressed and thus, it increases the incorporation of the envelope protein in the membranes surrounding the retrovirus-like particles. It is further preferred that cells expressing an envelope protein or a truncated envelope protein of a retrovirus also simultaneously express a Gag coding sequence of a retrovirus, as discussed above.

The present invention further provides immunogenic compositions comprising retrovirus-like particles made by the methods of the present invention, for administration to an animal, including a human, which is susceptible to infection by the cognate retrovirus. The immunogenic compositions of the present invention generally include a physiologically acceptable carrier, and advantageously further include component(s) which stimulate an immune response and/or enhance persistence at or near the site of administration. Where natural infection occurs at mucosal surfaces and where protective immunity is desired, administration of the immunogenic composition is accomplished by a route which favors the development of protective immunity at mucosal surfaces; a preferred route of administration is intranasal, oral, intragastric, vaginal, rectal or respiratory aerosol administration of the immunogenic composition. Where intranasal administration is the intended route of administration, it is advantageous to incorporate compounds which stimulate the development of mucosal immunity, e.g., the nontoxic cholera toxin B subunit, among others.

In addition to use in immunogenic compositions including vaccines, the VLPs of the present invention are useful in diagnostic methods such as those designed to detect antibody to the cognate virus. A serum sample or a sample of a mucosal secretion can be reacted with VLPs. Where the VLPs are affixed to a solid support, the sample can be added in a milieu suitable for antigen-antibody binding, and a labelled second antibody specific for sample antibody can be used to visualize instances of sample antibody binding to the immobilized particles. Suitable labels are well known to the art, and the skilled artisan can readily choose appropriate second antibody and/or modify the assay for particular application.

BRIEF DESCRIPTION OF THE DRAWINGS

FIGS. 2A–2C are electron micrographs of Sf9 cells infected with the Gag p56 recombinant (M.O.I. of 10). FIG. 2A shows budding of VLPs from the cell surface on the second day post infection. FIG. 2B shows particles released from the cells with the typical morphology of immature C-type retroviruses. FIG. 2C shows core-like structures in the cytoplasm of infected cells, some of which are multilayered. Magnification: FIG. 2A: 110,000. FIGS. 2B, 2C: 77,000.

FIGS. 3B, 3D and 3F correspond to the same recombinants coexpressed with a recombinant rBV Furin which expresses the protease furin (M.O.I of 10). Samples of cell lysate in 1 ml of RIP buffer (C) and all media (M) were collected after the pulse and at 10, 20 and 30 h chase and analyzed by immunoprecipitation and SDS-PAGE as described hereinbelow.

DETAILED DESCRIPTION OF THE INVENTION

The present invention provides methods for the production of virus-like particles (VLPs) carrying immunogenic envelope proteins, or truncated envelope proteins, of retroviruses, especially lentiviruses. Viruses whose envelope protein coding sequences can be adapted for expression in baculovirus expression systems, preferably *Autographa*

*californica* nuclear polyhedrosis virus (AcNPV) expression vectors in which the viral protein(s) is expressed under the regulatory control of a late or late/very late hybrid promoter, include, without limitation, HIV, SIV, feline immunodeficiency virus (FIV), feline leukemia virus, bovine immunodeficiency virus, bovine leukemia virus, equine infectious anemia virus, human T-cell leukemia virus and others. Incorporation of viral envelope proteins into the viral particles is significantly greater than in prior art VLPs, especially when the viral protein(s) is concomitantly expressed with a mammalian protease which efficiently cleaves the virus-encoded precursor proteins to mature proteins identical to or substantially similar to the corresponding viral structural proteins produced during a natural infection. Furin is an example of such a protease; preferably its coding sequence is also expressed from a late or late/very late baculovirus promoter. Other suitable proteases include convertin I (see, e.g., U.S. Pat. No. 5,541,062), the yeast precursor processing endoprotease KEX2 (see, e.g., Julius et al. (1994) and bacterial subtilisins (Hastrups et al. (1989) WO 89/06279).

Figure 1:
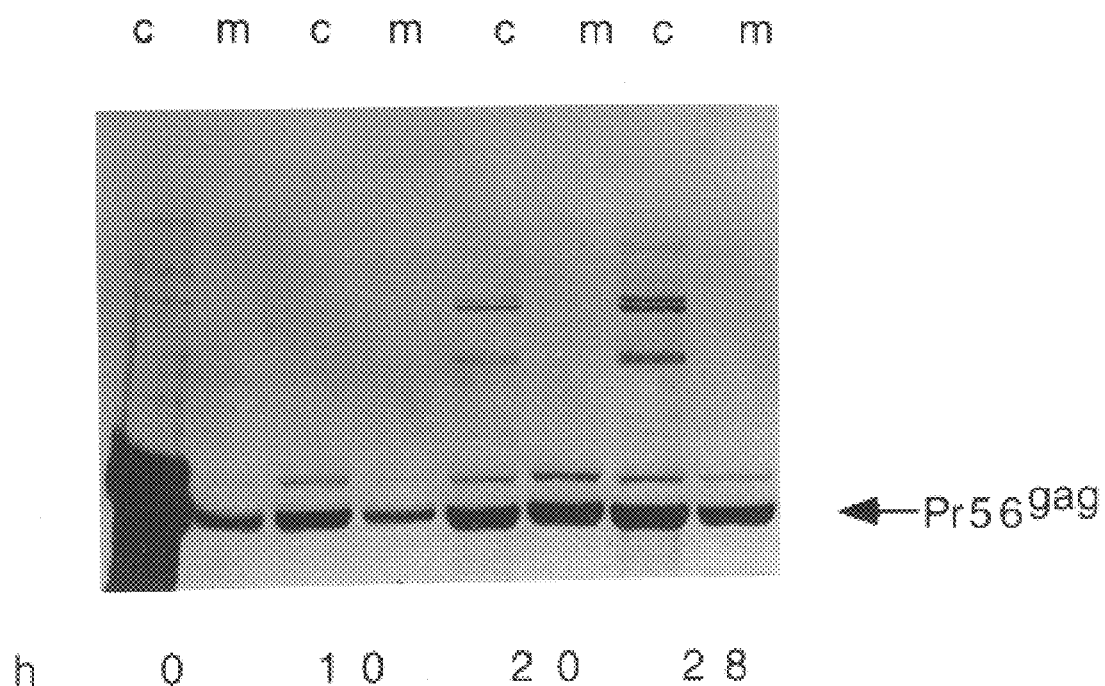
FIG. 1 illustrates Gag p56 expression and release into the media in a pulse-chase experiment. Sf9 cells were infected with the Gag p56 recombinant baculovirus at a multiplicity of infection (M.O.I.) of 10 and pulse labeled with [$^{35}$S] methionine for 1 h at 24 h post infection. All media (M) and cells as a lysate in 1 ml of RIP buffer (C) were collected after the pulse and at 10, 20, or 28 h chase and analyzed by immunoprecipitation as described hereinbelow.
Figure 3:
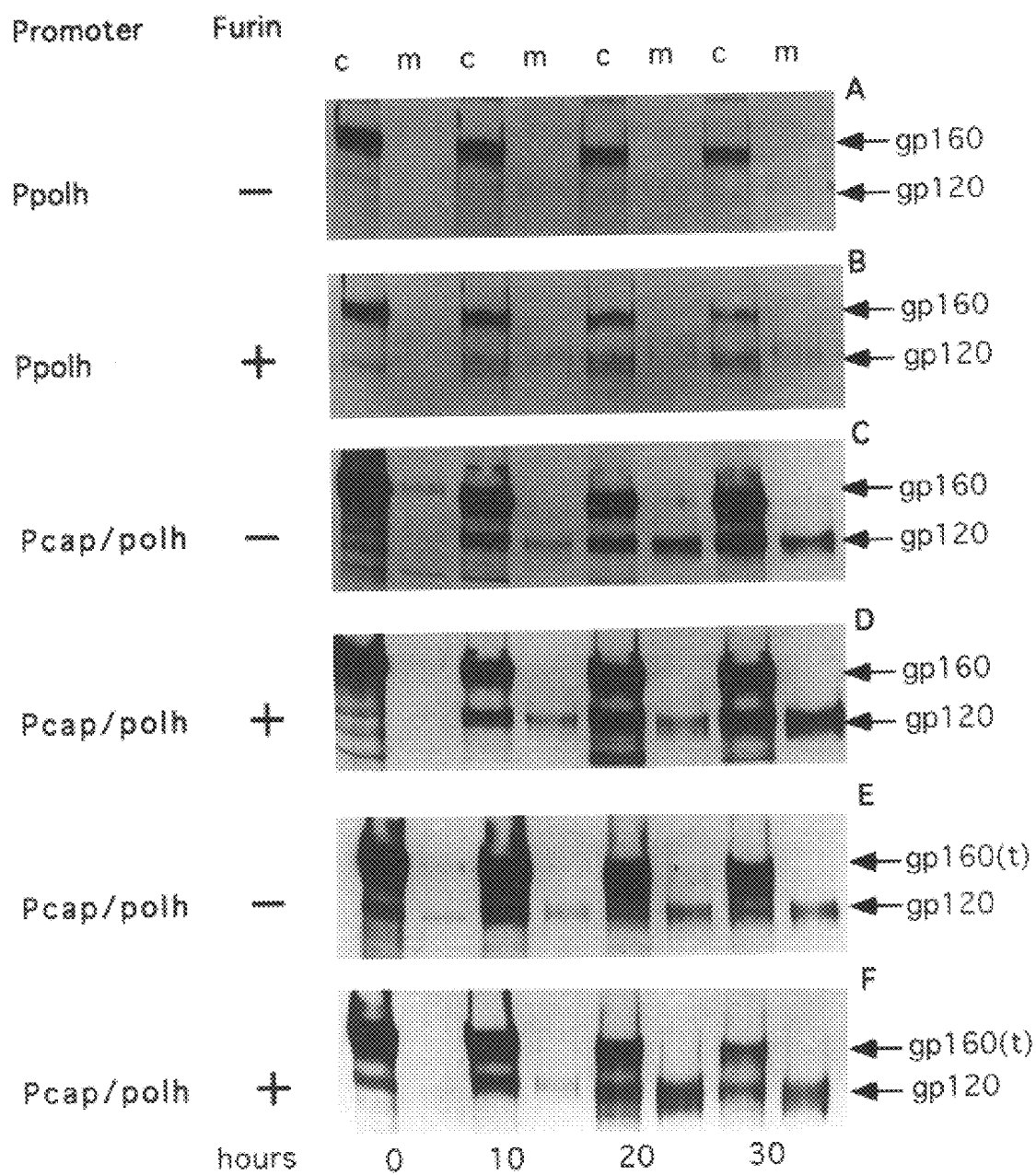
FIGS. 3A–3F illustrate SIV envelope protein expression in pulse-chase experiments. Sf9 cells were infected with rBV SIV Env (Ppolh) (FIG. 3A); rBV SIV Env(Pcap/polh) (FIG. 3C); or rBV SIV Env$_t$(Pcap/polh) (FIG. 3E) at a M.O.I. of 10 and radiolabeled for 1 h with [$^{35}$S] methionine at 24 h post infection.

The present application specifically exemplifies the production of immunogenic SIV retrovirus-like particles (VLPs) containing envelope and optionally other viral structural proteins but lacking any infectious viral nucleic acid. These VLPs are produced by incorporating the viral env coding sequence under the regulatory control of a late or hybrid late/very late baculovirus promoter, e.g., the cap/polh promoter, preferably with concomitant expression of a protease coding sequence (bovine furin, as specifically exemplified). Similar expression systems for other retroviruses including HIV, human T-cell leukemia type I virus, feline immunodeficiency virus, feline leukemia virus, equine infectious anemia virus, bovine immunodeficiency virus and bovine leukemia virus, among others, can be made without the expense of undue experimentation, using the guidance and teachings provided herein coupled with nucleotide sequence information readily accessible to the art.

To investigate the synthesis and assembly of the SIVmac239 Gag protein, Sf9 cells were infected with the Gag p56 recombinant at a M.O.I. of 10, and radiolabeled with [$^{35}$S] methionine at 24 h post infection. The synthesis of $Pr56^{gag}$ and its release into the culture medium are shown in FIG. 1. Significant amounts of $Pr56^{gag}$ were already detected in the medium in a 1 h pulse, indicating that assembly and release of antigens in Sf9 cells occur rapidly. By 20 h, increasing amounts of $Pr56^{gag}$ released into the media were detected. A decrease in the level of $Pr56^{gag}$ was reproducibly observed after chase periods, indicating instability of the protein.

To further investigate the assembly of $Pr56^{gag}$, Sf9 cells were infected with the Gag p56 recombinant and examined by electron microscopy. Budding of VLPs was observed from the cell surface on the second day post infection (FIG. 2A). At 30 h post infection particles with the typical morphology of immature C-type retroviral particles were not only budding at the cell surface, but also apparently released from cells (FIG. 2B). Some of the extracellular particles contained electron-dense granules, similar in appearance to cellular ribosomes, which represent an unusual feature for assembly of retroviruses. Formation of core-like structures occurred within the cytoplasm of infected cells. At higher magnification, in addition to core structures which appeared to be morphologically normal, some aberrant, multilayered core structures were observed (FIG. 2C). These results are consistent with a previous report (Delchambre et al., 1989) of assembly and release of $Pr56^{gag}$ in cells infected with recombinant baculoviruses.

A two-step procedure was developed for purification of the VLPs released from baculovirus-infected Sf9 cells, as described hereinbelow. The fraction with a density of 1.16 g/cm$^3$ corresponded to retrovirus-like particles (VLPs). Even partially purified preparations of VLPs obtained after pelleting through a sucrose cushion consisted mostly of the Pr56ma protein. The total protein yield for such crude VLPs preparations was about 15 mg/10$^9$ cells, and about 1 mg/10$^9$ cells (1 liter of culture) was recovered after further gradient purification.

It is known that the secretory pathways of insect cells are severely compromised at late times after baculovirus infection and that this prevents normal processing and secretion of some glycosylated proteins (Jarvis et al., 1990). Difficulties with the transport of viral envelope proteins may occur for the same reason. Therefore, expression under the control of an earlier (hybrid) promoter may enhance the levels of processing and transport of gp160 as compared with the very late polh promoter. To compare the expression patterns of the SIV Env glycoprotein, we used pulse-chase labeling experiments. The envelope recombinants including rBV SIV Env(Ppolh), and rBV SIV Env(Pcap/polh) expressed the precursor gp160 whereas the recombinant rBV SIV $Env_t$ (Pcap/polh) expressed the $gp160_t$ protein with a truncated cytoplasmic tail at high levels within cells (FIG. 3). In cells expressing SIV Env under control of the polyhedrin promoter, the Env protein precursor gp160 was not efficiently processed, and little or no protein was secreted into the culture media (FIG. 3A). In contrast, expression of Env (FIG. 3C) or $Env_t$ (FIG. 3E) under the control of the hybrid Pcap/polh promoter resulted in higher levels of expression, more efficient processing of the precursor proteins to gp120 and release of VLPs into the culture medium. Less than 1% of the envelope protein was detectable as gp120 in the cells or medium at any time point in FIG. 3A. With the hybrid promoter 40% of the envelope protein was found as cell-associated gp120 and 10% as gp120 in the medium after a 30 h chase. For $Env_t$ expressed with the hybrid promoter, 13% of the Env protein was cell-associated gp120, and 9% was secreted into the medium.

Krausslich et al., 1993 and Guo et al., 1990 reported that cleavage of HIV gp160 is important for its incorporation in virus particles and that infectious HIV-1 virus particles normally contain only the processed envelope glycoprotein. In mammalian cells intracellular sorting results in the transfer of most uncleaved gp160 to lysosomes, where it is degraded, while the cleaved precursor is transported to the cell surface and incorporated into the virus (Willey et al., 1988).

Furin is a mammalian subtilisin-like protease which is membrane-associated and cleaves the HIV-1 envelope protein upon expression in mammalian cells (Hallenberger et al., 1992). Although there is evidence that insect cells contain a furin-like protease (Kuroda et al., 1986), gp160 of HIV-1 is not cleaved in these cells (Morikawa et al., 1993). Thus, it appears that either gp160 is a poor substrate for the insect protease or that the two proteins otherwise fail to interact in insect cells.

We have investigated the effect of coexpressed bovine furin with Env on processing of gp160 and the expression of gp120 on the cell surface. Expression of the protease furin was confirmed by immunoprecipitation with a rabbit polyclonal antiserum against the human furin protease. Two bands of ~100 and ~90 kB were detected in cell lysate and the product was stable up to 30 h chase (54 h post infection). The results of pulse-chase labeling experiments for Env recombinants coexpressed with furin are shown in FIGS.

3A–3F. Co-expression with furin increases secretion of the processed form of the SIV envelope protein upon expression in Sf9 cells for all recombinants. After the 30 h chase, a 2-fold increase in the level of secretion of gp120 was seen (compare FIG. 3D to FIG. 3C), and a 4.5-fold increase was seen (compare FIGS. 3F and 3E). Therefore, the most effective system for processing and secretion of the Env protein was the use of the hybrid late/very late promoter and co-expression with furin.

Figure 4:
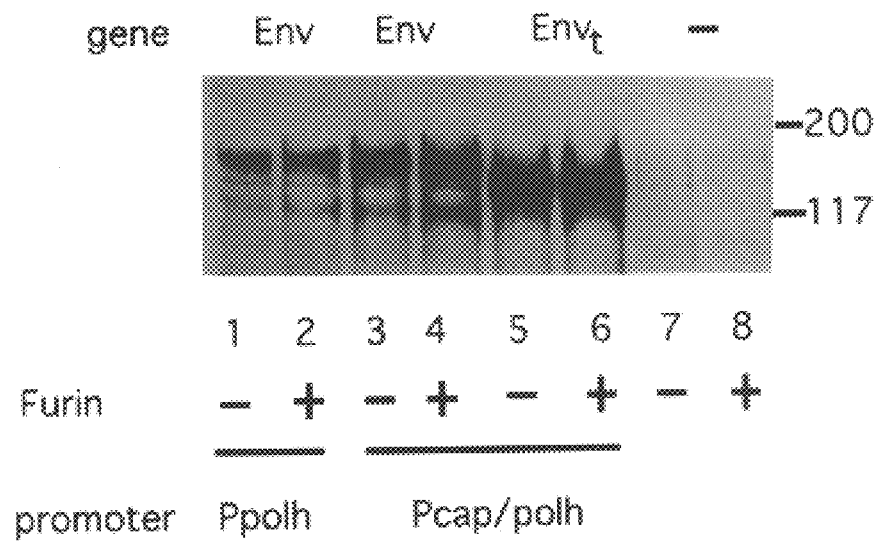
FIG. 4 shows surface biotinylation of Sf9 cells infected with rBV SIV Env(Ppolh) (lane 1), rBV SIV Env(pc/pS1) (lane 3), rBV SIV Env$_t$(pc/pS1) (lane 5). Lanes 2, 4 and 6 show the result of surface biotinylation when the corresponding Env expressing recombinants were coinfected with a recombinant expressing the protease furin. Lane 7, control of wild type *Autographa californica* nucleopolyhedrosis virus (AcNPV, baculovirus) infected cells; lane 8, coinfection of wild type virus with the furin expressing recombinant. A M.O.I. of 10 was used for all recombinants. Biotinylation was done at 24 h post infection followed by immunoprecipitation, SDS-PAGE, and Western blot as described in the Examples.

Upon expression in mammalian cells the major fraction of the uncleaved precursor gp160 is transported to and degraded within lysosomes. A small fraction of gp160 is cleaved by furin or a cellular protease of similar substrate specificity to the surface gp120 and membrane-associated gp41 subunits which are transported to the cell surface and incorporated into the virus. We used surface fluorescence and surface biotinylation to determine whether the Env protein is transported to the cell surface and thus available for incorporation into VLPs in insect cells. Env precursor and some gp120 appeared on the surface of infected Sf9 cells between 17 and 23 h post infection (FIG. 4). The total level of surface expression of Env was 1.9-fold higher when the earlier promoter was used (lane 3) and 2.6-fold higher with $Env_t$ expression (lane 5) in comparison to Env expression under the Polh promoter (lane 1). The truncated form of the envelope glycoprotein (lane 5) also shows a 1.5-fold higher level of the unprocessed precursor on the cell surface than does the full length Env (lane 3). Co-expression with furin increased the amount of gp120 on the cell surface for all recombinants (lane 4, 70% increase over lane 3).

Figure 5:
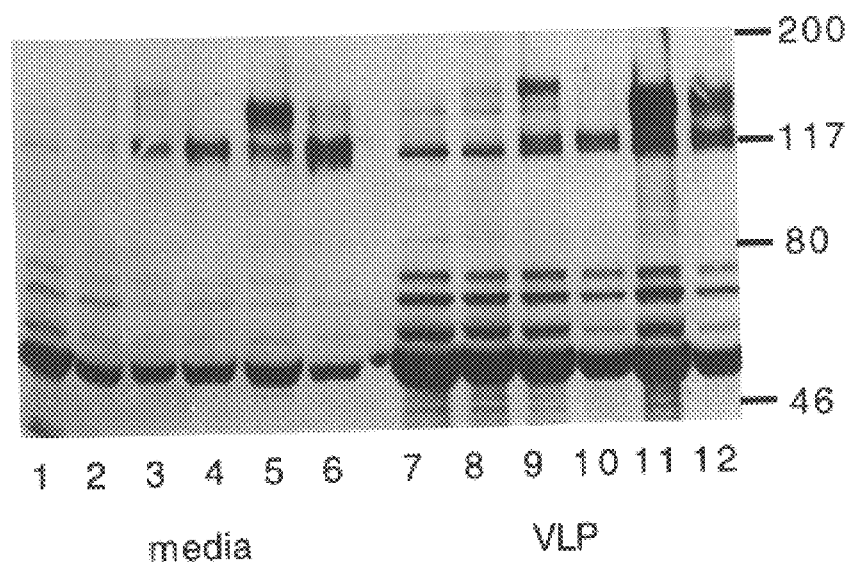
FIG. 5 provides a comparison of the proteins released into the media (lanes 1–6) and those incorporated into VLPs (lanes 7–12) after infection with different recombinants. Sf9 cells in 60 mm dishes were infected with the Gag p56 recombinant (M.O.I. of 7), and one of the Env expressing recombinants (M.O.I. of 10) with or without the furin recombinant (M.O.I. of 10). Cells were continuously labeled starting from 24 h post infection as described hereinbelow. Media (4 ml aliquots) were collected at 3 days post infection and preclarified by low speed centrifugation. Aliquots of 1 ml of the media were analyzed by immunoprecipitation, and the rest (3 ml) were pelleted through a sucrose cushion, as described hereinbelow. Lanes 1 and 7 show proteins immunoprecipitated from medium and pelleted material for Sf9 cells infected only with Gag p56; 2 and 8, Gag p56 and rBV SIV Env(Ppolh); 3 and 9, Gag p56 and rBV SIV Env(Pcap/polh); 4 and 10, the same recombinants as 3 and 9 coinfected with the furin recombinant; 5 and 11, Gag p56 and rBV SIV Env$_t$(Pcap/polh); 6 and 12, the same as 5 and 11 together with the furin recombinant.

To determine optimal conditions for incorporation of Env into VLPs, we infected SF9 cells with the Gag p56 recombinant and different Env-expressing recombinants with or without furin expressed in trans. FIG. 5 shows SIV-related proteins incorporated into VLPs purified by centrifugation through a sucrose cushion. Different sets of recombinant baculovirus expression vectors were used for coinfections, and infected cells were continuously labeled for two days. Lanes 1–6 show proteins immunoprecipitated from the medium, and lanes 7–12 show the VLPs pelleted through a 20% sucrose cushion. No Env could be detected in the VLPs when pPolh was used to control expression. When the Pcap/polh promoter was used for Env (lane 9) as well as $Env_t$ expression (lane 11), the VLP preparations were observed to contain the envelope protein, some of which had undergone proteolytic cleavage. Coexpression with furin increased the level of secretion of gp120 into the media 3-fold for Env (comparing lanes 3 and 4) and 2-fold for $Env_t$ (comparing lanes 5 and 6). Although the recovery of total Env proteins in VLPs was decreased in the presence of furin, the ratios of the gp120 to the uncleaved precursors for both Env and $Env_t$ were increased. The percent of cleaved Env protein was: lane 9, 32%; lane 10, 100%; lane 11, 24%; lane 12, 37%. Surprisingly, coexpression with Env increased the release of the Gag in a pelletable form from 47% (comparing lanes 1 and 7) up to 100% (comparing lanes 6 vs. 12 or 3 vs. 9) when Gag and Env proteins were expressed together.

Figure 6:
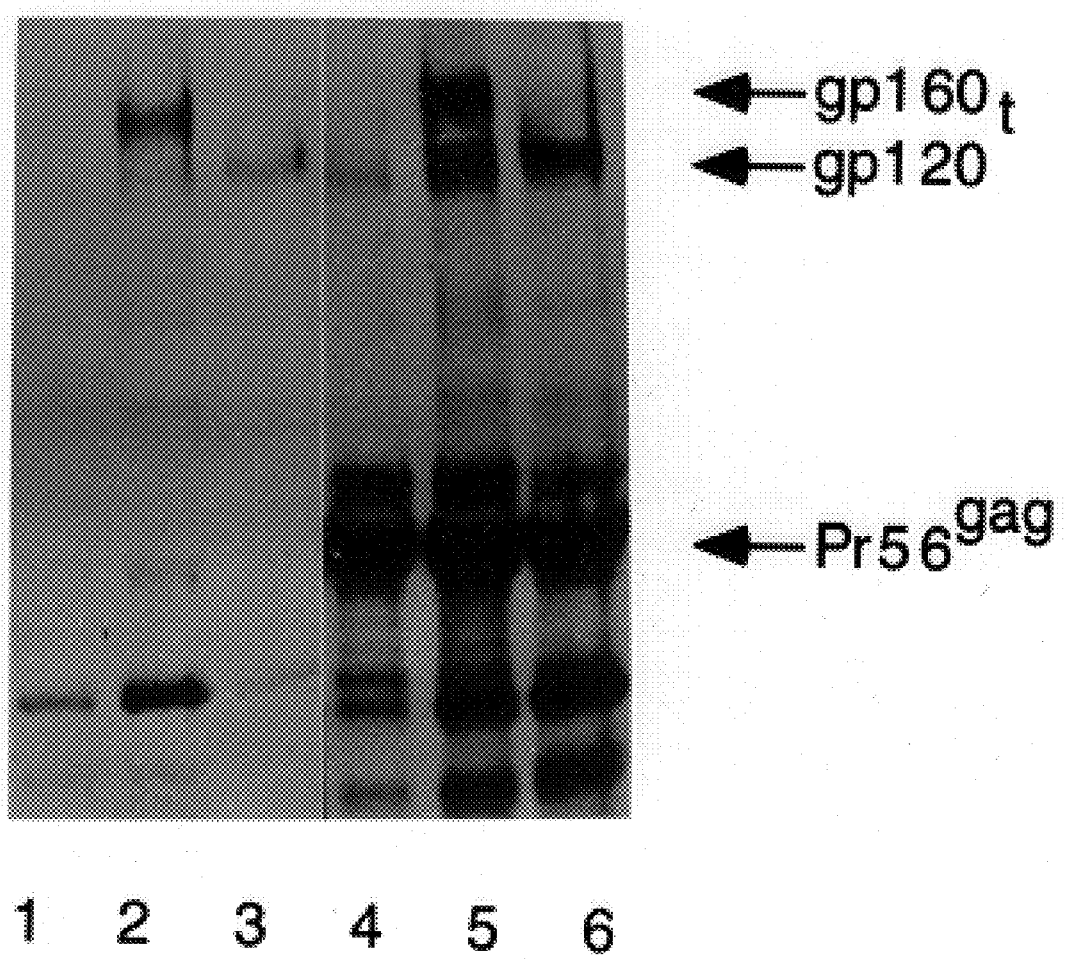
FIG. 6 provides a comparison of the amount of Env protein secreted into the medium in pelletable form upon expression alone or coexpressed with Gag p56. Sf9 cells in 60 mm dishes were infected with recombinant baculoviruses expressing SIV Env or SIV Env$_t$ alone (lanes 1–3), or coinfected with the Gag precursor expressing recombinant (lanes 4–6). Lanes 1 and 4 show infection with rBV SIV Env(Pcap/polh) and furin recombinants; lanes 2 and 5, infection with rBVSIV Env$_t$(Pcap/polh); lanes 3 and 6, the same as 2 and 5 together with the furin recombinant. Cells were continuously labeled starting from 24 h post infection as described hereinbelow. Media samples were collected at 3 days post-infection and preclarified by low speed centrifugation. 3 ml aliquots of the media were pelleted through a sucrose cushion, and pelleted material was analyzed by immunoprecipitation as described in the Examples.
Figure 7:
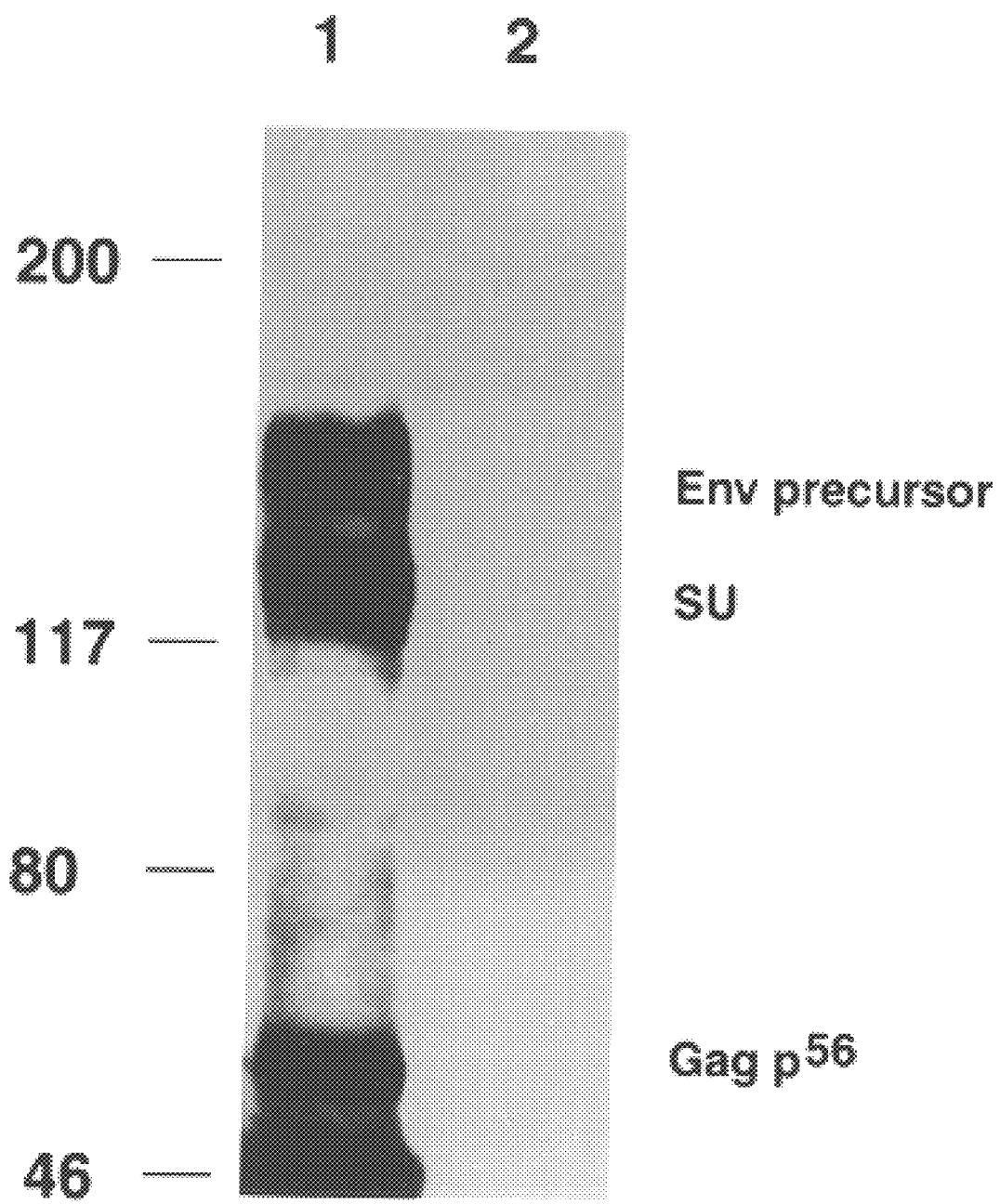
FIG. 7 shows the reactivity of SIV Env in virus-like particles with rhesus monkey antibody. Sf9 cells were infected with rBV SIX Gag p56 at a multiplicity of infection of 7 and with rBV SIV Env$_t$ at a multiplicity of 10. Supernatant was collected 2 days after infection. VLPs were collected and purified. Samples were solubilized and loaded in lane 1. Vane 2 was loaded with control supernatant collected from wild-type baculovirus infection. Western blot analysis was carried out by incubating with primary rhesus monkey antibody to SIV at a 1:2000 dilution and secondary rabbit anti-monkey antibody conjugated with control horseradish peroxidase at a 1:2000 dilution. Proteins were detected by enhanced chemiluminescence. Positions of molecular weight markers (in kDa) are marked at the left, and the positions of the Env precursor, SU (gp 120) and Gag p56 are marked on the right.

It was previously reported (Krausslich et al., 1993) for expression in mammalian cells, and we observed upon expression in insect cells, that a fraction of the Env glycoprotein can be released into the medium in membranous fragments, especially later in infection. It was therefore important to determine that our preparations contain the Env protein specifically incorporated in VLPs, rather than in membrane fragments which may co-purify with VLPs. For this purpose, we compared the release of the Env protein in a pelletable form when expressed by itself or upon coinfection with Gag. Sf9 cells were infected with Env expressing recombinants alone or coinfected with the Gag p56 recombinant, and Env expressing recombinants. After two days of continuous labeling, media were collected, preclarified at low speed and loaded onto a sucrose cushion. FIG. 6 shows proteins immunoprecipitated from pelletable material when Sf9 cells were infected with a recombinant expressing $Env_t$ alone (lane 2), coinfected with furin and Env recombinants (lane 1), or with furin and $Env_t$ recombinants (lane 3). Lanes 5, 4, and 6, respectively, show results for the same sets of recombinants coexpressed with $Pr56^{gag}$. Comparison of the protein profiles of the pelleted material demonstrates that only the $Env_t$ recombinant shows pelletable $gp160_t$ protein released in the absence of Gag, and all three recombinants show greatly increased levels of pelletable Env proteins when coexpressed with Gag proteins.

When coexpressed with Gag, the total Env recovered in a pelletable form was increased 1.7-fold for $Env_t$ (comparing lanes 2 and 5) and 3-fold for $Env_t$ when coexpressed with furin (comparing lanes 3 and 6). The resulting preparations of particles contained some gp120 even when furin was not present in the system; however, furin effects more extensive cleavage of the envelope proteins. In lane 5, 53% of the Env was present in an uncleaved form, whereas in lane 6 only 25% remained in the uncleaved form. The truncated $Env_t$ protein (lanes 5 and 6) shows significant advantages in comparison with the full length protein (lane 4) in the level of its incorporation in VLPs when coexpressed with the Gag precursor (lane 4 vs. lane 5, a 10-fold increase) as well as when coexpressed with Gag and furin (lane 4 vs. lane 6, a 6-fold increase).

SIV virus-like particles consisting of the Gag precursor protein as well as the Env protein can be produced using a baculovirus expression system. The production of defective lentivirus particles was previously reported in several recombinant expression systems, including vaccinia virus (Haffar et al., 1990), fowlpox virus (Jenkins et al., 1991), baculovirus (Delchambre et al., 1989; Luo et al., 1990), SV40 (Lee and Linial, 1994) and in stable cell lines (Krausslich et al., 1993; Haynes et al., 1991; Rovinski et al., 1992). The matrix (MA) protein of retroviruses plays an important role in virus assembly by directing the transport and membrane association of Gag precursor (Yuan et al., 1993; Zhou et al., 1994), and is also critical for the incorporation of Env glycoproteins into virions (Yu et al., 1992; Wang et al., 1993; Lee and Linial, 1994; Dorfman et al., 1994). Conditions for targeted incorporation of Env into VLPs in various recombinant systems appear to be very system and cell type dependent. For example, transient cotransfection of plasmids directing HIV-1 Gag and Env expression did not yield specific glycoprotein incorporation in one report (Krausslich et al., 1993) but others were successful using a similar approach (Dong and Hunter, 1993; Lee and Linial, 1994).

Passage of some lentiviruses in cell lines of different origins selects for preferential growth of viruses with a premature stop codon in the cytoplasmic tail of the envelope glycoprotein (Hirsch et al., 1989). Truncation of the SIV and HIV-2 envelope protein cytoplasmic domains occurs upon propagation of these viruses in human cell lines, and significantly enhances the envelope protein density on released particles as well as envelope-mediated cell fusion activity (Mulligan et al., 1992; Zingler and Littman, 1993; Spies et al., 1994; Ritter et al., 1993). In the present study, we observed that a truncated form of the SIV Env protein was also transported more efficiently to the cell surface and incorporated into VLPs at higher levels in insect cells than the full length Env protein. The truncated Env proteins therefore appear to possess functional advantages even in the heterologous insect cell system.

Cleavage of the Env protein by a cellular protease is essential for the production of infectious virus (McCune et al., 1988; Guo et al., 1990; Krausslich et al., 1993). In some previous reports, only cleaved glycoproteins were present in purified particles (Yu et al., 1992; Haffar et al., 1990; Krausslich et al., 1993; Haynes et al., 1991; Rovinski et al., 1992). However, others have reported the presence of precursor as well as the processed form of envelope glycoprotein in VLPs (Jenkins et al., 1991; Lee and Linial, 1994; Page et al., 1992; Vzorov et al., 1991). This may be due in part to copurification of the particles with membrane vesicles (Krausslich et al., 1993) or by a relatively slow rate of envelope glycoprotein cleavage in some cell lines (Page et al., 1992). In the present study, we observed incorporation of uncleaved gp160, proteins into VLPs, but the full length Env protein was recovered almost exclusively in the cleaved form. Thus, the nature of the Env construct may also play a role in determining whether uncleaved precursors are incorporated into VLPs.

The formation of immature retrovirus-like particles has been investigated in detail by expression of the Gag precursor and various mutants in baculovirus expression systems (Delchambre et al., 1989; Overton et al., 1989; Luo et al., 1990). It has been shown that the unprocessed Gag precursor can spontaneously assemble into particles in the absence of other viral proteins. Myristylation of the N-terminal glycine residue is necessary for its association with the plasma membrane, budding and extracellular release of VLPs (Chazal et al., 1995). Extension of an expression cassette to include the viral protease coding region leads to intracellular Gag processing, and particle formation in insect cells was not observed under these conditions (Morikawa et al., 1991; Hughes et al., 1993). In contrast to the release of VLPs containing Gag proteins, HIV envelope glycoproteins remain mainly cell-associated and inefficiently processed upon expression in insect cells (Rusche et al., 1987; Wells and Compans, 1990). Envelope glycoprotein incorporation into VLPs has therefore been problematic in the baculovirus expression system. Concerns have been expressed about the immunogenic properties of subunit vaccines based on baculovirus-expressed HIV envelope glycoproteins (Moore et al., 1993). The reduced immunogenicity of baculovirus-expressed HIV-1 envelope preparations can be explained by their denaturation during purification from cells, since native, but not denatured, recombinant HIV-1 gp120 generates a protective immune response (Haigwood et al., 1992). It has also been demonstrated that the mammalian subtilisin-like protease furin can cleave the HIV envelope glycoprotein produced in insect cells (Morikawa et al., 1993). In the present study, utilization of an earlier hybrid pCap/Polh promoter for Env expression and providing the protease furin in trans enabled us to deliver processed Env proteins to the cell surface at earlier times post infection, and to successfully incorporate these envelope proteins into budding particles. This approach may be useful for further studies of virus assembly as well as for production of antigens for experimental vaccines.

As used herein, a protease (peptidase) is an enzyme which catalyzes the hydrolysis of peptide bonds (or other amide bonds) in protein substrates.

A vector is a genetic unit (or replicon) to which or into which other DNA segments can be incorporated to effect replication, and optionally, expression of the attached segment. Examples include plasmids, cosmids, viruses, chromosomes and minichromosomes. Particularly preferred expression vectors (for expression of an attached segment) are baculovirus vectors, especially those derived from AcNPV.

A coding sequence is a nucleotide sequence that is transcribed into mRNA and translated into protein, in vivo or in vitro.

Regulatory sequences are nucleotide sequences which control transcription and/or translation of the coding sequences which they flank.

Processing sites are described in terms of nucleotide or amino acid sequences (in context of a coding sequence or a polypeptide). A processing site in a polypeptide or nascent peptide is where proteolytic cleavage occurs, where glycosylation is incorporated or where lipid groups (such as myristoylation) occurs. Proteolytic processing sites are where proteases act.

Virus-like particles, or retrovirus-like particles, in the context of the present application, are membrane-surrounded structures comprising viral envelope proteins embedded within the membrane of the host cell in which they are produced, and preferably, additional viral core proteins in the VLPs. These VLPs do not contain intact viral nucleic acid, and they are non-infectious. Desirably, there is sufficient envelope protein on the surface of the VLP so that when a VLP preparation is formulated into an immunogenic composition and administered to an animal or human, an immune response (cell-mediated or humoral) is raised. Desirably, the Env protein is truncated from the carboxy terminus as compared with the naturally occurring virus envelope protein. In the context of the present invention, a "truncated" envelope protein is one which contains less than a full length cytoplasmic domain, which but retains surface antigenic determinants against which an immune response is generated, preferably a protective immune response, and it retains sufficient envelope sequence for proper precursor processing and membrane insertion. The skilled artisan can produce truncated virus envelope proteins using recombinant DNA technology and virus coding sequences which are readily available to the public. For example, the coding sequence of a virus envelope protein can be engineered for expression in a baculovirus expression vector, for example, using a commercially available baculovirus vector, under the regulatory control of a virus promoter, with appropriate modifications of the sequence to allow functional linkage of the coding sequence to the regulatory sequence, and truncation (deletion) of the portion of the coding sequence which encodes the cytoplasmic domain of the envelope protein, again with appropriate translation stop signals and sequences which allow operable splicing of the truncated envelope and associated sequences into the vector. A specifically exemplified truncated SIV envelope protein lacks the 89 amino acids at the carboxy terminus of the naturally occurring SIV envelope protein.

In the context of the present invention, truncation of the envelope protein is from the carboxy terminus of the envelope protein. Contemplated are truncated envelope proteins retaining from about 0% to about 90% of the cytoplasmic domain (where the cytoplasmic domain is the region between the C-terminus of the transmembrane domain and the C-terminus of the entire envelope protein). Preferably from about 10 to about 25% of the cytoplasmic domain is retained. Also encompassed by "truncated," are all percentages and ranges, within the 5 to 90% range, including from abou 15% to about 50%.

VLPs based on cloned retroviral envelope proteins, and preferably further comprising Gag proteins from the same retroviruses, can be readily produced without the expense of undue experimentation by the ordinary skilled artisan using the teachings of the present application taken with baculovirus vectors and what is well known to and readily accessible to the art. Sequence information is known for feline leukemia virus (see, e.g., Boomer et al., 1994; Rohn et al. 1994, and references cited in both of the foregoing), feline immunodeficiency virus (see, e.g., Pancino et al., 1993 and references cited therein), bovine immunodeficiency virus (see, e.g., Chen et al., 1994, and references cited therein), human T-cell leukemia virus type I (see., e.g., Wang et al., 1993; Pique et al., 1990; Vile et al., 1991, and references cited in the foregoing references), bovine leukemia virus (see, e.g., Oroszlan et al., 1984; Sagata and Ikawa, 1984); and equine infectious anemia virus (see, e.g., Cunningham et al., 1993; Schiltz et al., 1992; Ball et al., 1992; Rushlow et al., 1986; and references cited in the foregoing).

In another embodiment, polyclonal and/or monoclonal antibodies capable of specifically binding to a retrovirus or lentivirus or fragments thereof are provided. The term antibody is used to refer both to a homogenous molecular entity, or a mixture such as a serum product made up of a plurality of different molecular entities. Monoclonal or polyclonal antibodies which specifically react with the virus-like particles of the present invention may be made by methods known in the art. See, e.g., Harlow and Lane (1988) *Antibodies: A Laboratory Manual,* Cold Spring Harbor Laboratories; Goding (1986) *Monoclonal Antibodies: Principles and Practice,* 2d ed., Academic Press, New York; and Ausubel et al. (1987) supra. Also, recombinant immunoglobulins may be produced by methods known in the art, including but not limited to, the methods described in U.S. Pat. No. 4,816,567. Monoclonal antibodies with affinities of $10^8$ $M^{-1}$, preferably $10^9$ to $10^{10}$ or more, are preferred.

Antibodies specific for retrovirus-like particles and envelope proteins of retroviruses may be useful, for example, as probes for screening DNA expression libraries or for detecting the presence of the cognate retrovirus in a test sample. Frequently, the polypeptides and antibodies will be labeled by joining, either covalently or noncovalently, a substance which provides a detectable signal. Suitable labels include but are not limited to radionuclides, enzymes, substrates, cofactors, inhibitors, fluorescent agents, chemiluminescent agents, magnetic particles and the like. United States Patents describing the use of such labels include but are not limited to U.S. Pat. Nos. 3,817,837; 3,850,752; 3,939,350; 3,996,345; 4,277,437; 4,275,149; and 4,366,241.

Antibodies specific for retrovirus-like particles and retroviral envelope proteins may be useful in treating animals, including humans, suffering from the cognate retroviral disease. Such antibodies can be obtained by the methods described above and subsequently screening the env-specific antibodies for their ability to inhibit virus uptake by target cells.

Compositions and immunogenic preparations, including vaccine compositions, comprising the retrovirus-like particles of the present invention and capable of inducing protective immunity in a suitably treated animal or human and a suitable carrier therefor are provided. Immunogenic compositions are those which result in specific antibody production or in cellular immunity when injected into a human or an animal. Such immunogenic compositions or vaccines are useful, for example, in immunizing an animal, including a human, against infection and/or damage caused by retroviruses, including but not limited to, HIV, human T-cell leukemia virus (HTLV) type I, SIV, FIV, bovine immunodeficiency virus, bovine leukemia virus and equine infectious anemia virus, among others. The vaccine preparations comprise an immunogenic amount of one or more retrovirus-like particles fragment(s) or subunit(s) thereof. Such vaccines may comprise one or more retrovirus envelope proteins and/or truncated envelope proteins on the surfaces of the retrovirus-like particles, or in combination with another protein or other immunogen, such as one or more additional virus components naturally associated with viral particles or an epitopic peptide derived therefrom. By "immunogenic amount" is meant an amount capable of eliciting the production of antibodies directed against the retrovirus, in a mammal to which the vaccine has been administered. It is preferred for SIV, HIV and HTLV, among others, that the route of administration and the immunogenic composition is designed to optimize the immune response on mucosal surfaces, for example, using nasal administration (via an aerosol) of the immunogenic composition.

Immunogenic carriers can be used to enhance the immunogenicity of the retrovirus-like particles, env and other components or peptides derived in sequence from any of the foregoing retroviruses. Such carriers include but are not limited to proteins and polysaccharides, microspheres formulated using, e.g., a biodegradable polymer such as DL-lactide-coglycolide, liposomes, and bacterial cells and membranes. Protein carriers may be joined to the proteinases or peptides derived therefrom to form fusion proteins by recombinant or synthetic means or by chemical coupling. Useful carriers and means of coupling such carriers to polypeptide antigens are known in the art.

The immunogenic compositions and/or vaccines may be formulated by any of the means known in the art. They can be typically prepared as injectables or as formulations for intranasal administration, either as liquid solutions or suspensions. Solid forms suitable for solution in, or suspension in, liquid prior to injection or other administration may also be prepared. The preparation may also, for example, be emulsified, or the protein(s)/peptide(s) encapsulated in liposomes. Where mucosal immunity is desired, the immunogenic compositions advantageously contain an adjuvant such as the nontoxic cholera toxin B subunit (see, e.g., U.S. Pat. No. 5,462,734). Cholera toxin B subunit is commercially available, for example, from the Sigma Chemical Company, St. Louis, Mo. Other suitable adjuvants are available and may be substituted therefor. It is preferred that an adjuvant for an aerosol immunogenic (or vaccine) formulation is able to bind to epithelial cells and stimulate mucosal immunity.

Among the adjuvants suitable for mucosal administration and for stimulating mucosal immunity are organometallopolymers including linear, branched or cross-linked silicones which are bonded at the ends or along the length of the polymers to the particle or its core. Such polysiloxanes can vary in molecular weight from about 400 up to about 1,000,000 daltons; the preferred length range is from about 700 to about 60,000 daltons. Suitable functionalized silicones include (trialkoxysilyl) alkyl-terminated polydialkylsiloxanes and trialkoxysilyl-terminated polydialkylsiloxanes, for example, 3-(triethyoxysilyl) propyl-terminated polydimethylsiloxane. See U.S. Pat. No. 5,571,531, incorporated by reference herein. Phosphazene polyelectrolytes can also be incorporated into immunogenic compositions for transmucosal administration (intranasal, vaginal, rectal, respiratory system by aerosol administration) (See e.g., U.S. Pat. No. 5,562,909).

The active immunogenic ingredients are often mixed with excipients or carriers which are pharmaceutically acceptable and compatible with the active ingredient. Suitable excipients include but are not limited to water, saline, dextrose, glycerol, ethanol, or the like and combinations thereof. The concentration of the immunogenic polypeptide in injectable, aerosol or nasal formulations is usually in the range of 0.2 to 5 mg/ml. Similar dosages can be administered to other mucosal surfaces.

In addition, if desired, the vaccines may contain minor amounts of auxiliary substances such as wetting or emulsifying agents, pH buffering agents, and/or adjuvants which enhance the effectiveness of the vaccine. Examples of adjuvants which may be effective include but are not limited to: aluminum hydroxide; N-acetyl-muramyl-L-threonyl-D-isoglutamine (thr-MDP); N-acetyl-nor-muramyl-L-alanyl-D-isoglutamine (CGP 11637, referred to as nor-MDP); N-acetylmuramyl-L-alanyl-D-isoglutaminyl-L-alanine-2-(1'-2'-dipalmitoyl-sn-glycero-3hydroxyphosphoryloxy)-ethylamine (CGP 19835A, referred to as MTP-PE); and RIBI, which contains three components extracted from bacteria: monophosphoryl lipid A, trehalose dimycolate and cell wall skeleton (MPL+TDM+CWS) in a 2% squalene/Tween 80 emulsion. The effectiveness of an adjuvant may be determined by measuring the amount of antibodies (especially IgG, IgM or IgA) directed against the immunogen resulting from administration of the immunogen in vaccines which comprise the adjuvant in question. Such additional formulations and modes of administration as are known in the art may also be used.

SIV or HIV virus-like particles and/or epitopic fragments or peptides of sequences derived from one or more of those or from other retrovirus proteins having primary structure similar (more than 90% identity) to pathogenic retrovirus proteins may be formulated into vaccines as neutral or salt forms. Pharmaceutically acceptable salts include but are not limited to the acid addition salts (formed with free amino groups of the peptide) which are formed with inorganic acids, e.g., hydrochloric acid or phosphoric acids; and organic acids, e.g., acetic, oxalic, tartaric, or maleic acids. Salts formed with the free carboxyl groups may also be derived from inorganic bases, e.g., sodium, potassium, ammonium, calcium, or ferric hydroxides, and organic bases, e.g., isopropylamine, trimethylamine, 2-ethylaminoethanol, histidine, and procaine.

The immunogenic compositions or vaccines are administered in a manner compatible with the dosage formulation, and in such amount and manner as will be prophylactically and/or therapeutically effective, according to what is known to the art. The quantity to be administered, which is generally in the range of about 100 to 1,000 µg of protein per dose, more generally in the range of about 5 to 500 µg of protein per dose, depends on the subject to be treated, the capacity of the individual's (or animal's) immune system to synthesize antibodies, and the degree of protection desired. Precise amounts of the active ingredient required to be administered may depend on the judgment of the physician or veterinarian and may be peculiar to each individual, but such a determination is within the skill of such a practitioner.

The vaccine or other immunogenic composition may be given in a single dose; two dose schedule, for example two to eight weeks apart; or a multiple dose schedule. A multiple dose schedule is one in which a primary course of vaccination may include 1 to 10 or more separate doses, followed by other doses administered at subsequent time intervals as required to maintain and/or reinforce the immune response, e.g., at 1 to 4 months for a second dose, and if needed, a subsequent dose(s) after several months. Humans (or other animals) immunized with the retrovirus-like particles of the present invention are protected from infection by the cognate retrovirus.

Except as noted hereafter, standard techniques for peptide synthesis, cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook et al. (1989) *Molecular Cloning,* Second Edition, Cold Spring Harbor Laboratory, Plainview, N.Y.; Maniatis et al. (1982) *Molecular Cloning,* Cold Spring Harbor Laboratory, Plainview, N.Y.; Wu (ed.) (1993) Meth. Enzymol. 218, Part I; Wu (ed.) (1979) Meth. Enzymol. 68; Wu et al. (eds.) (1983) *Meth. Enzymol.* 100 and 101; Grossman and Moldave (eds.) *Meth. Enzymol.* 65; Miller (ed.) (1972) *Experiments in Molecular Genetics,* Cold Spring Harbor Laboratory, Cold Spring Harbor, N.Y., Old Primrose (1981) *Principles of Gene Manipulation,* University of California Press, Berkeley; Schleif and Wensink (1982) *Practical Methods in Molecular Biology;* Glover (ed.) (1985) *DNA Cloning* Vol. I and II, IRL Press, Oxford, UK; Hames and Higgins (eds.) (1985) *Nucleic Acid Hybridization,* IRL Press, Oxford, UK; Setlow and Hollaender (1979) *Genetic Engineering: Principles and Methods,* Vols. 1–4, Plenum Press, N.Y. Abbreviations and nomenclature, where employed, are deemed standard in the field and commonly used in professional journals such as those cited herein. All references and patents cited in the present application are hereby incorporated by reference in their entirety.

The foregoing discussion and the following examples illustrate but are not intended to limit the invention. The skilled artisan will understand that alternative methods may be used to implement the invention.

EXAMPLES

Example 1

Cells and Viruses

*Spodoptera frugiperda* Sf9 cells were maintained in serum free SF900 II medium (Gibco BRL) in suspension. Stirrer bottles with 50–250 ml capacity were used to grow cells and to produce virus stocks. Titers of stocks were determined by plaque assay (O'Reilly et al., 1992).

Example 2

Construction of Recombinant Transfer Vectors

Two AcNPV transfer vectors were used: pAcYM1, which facilitates the generation of nonoccluded (Occ$^-$)recombinant virus expressing a heterologous gene under the control of the polyhedrin (Ppolh) promoter and pc/pS1, in which expression is under the control of a hybrid capsid/polyhedrin promoter (Pcap/polh). The pc/pS1 plasmid was provided by Dr. Lois K. Miller (University of Georgia, Athens). The sequence of the Cap/polh promoter is given in Thiem and Miller, 1990. A DNA fragment encoding the SIV envelope protein precursor gp160 was excised from the pTSE54 plasmid as described earlier (Ritter et al., 1993) and ligated into the BamH1 site of pAcYM1, and in the SmaI site of pc/pS1. To obtain a recombinant virus expressing a truncated form of the Env protein, a stop codon in position 8803 was transferred from plasmid pSpE3'/TMstop, provided by T. Kodama (Ritter et al., 1993), by exchanging ClaI-BglII restriction fragments derived from this plasmid with the corresponding full length Env construct. A recombinant baculovirus expressing full length Pr56$^{gag}$ was obtained using the pAcYM1 transfer vector. A KpnI-BstEII fragment of the original pSPSPGP plasmid (obtained from Dr. Patrick B. Johnston, University of Alabama at Birmingham) encoding the Gag-Pol region of SIVmac239 was treated with Bal31 exonuclease, then with Klenow polymerase, and subcloned in pGEM 11Z. After sequence analysis, an EcoRI-BspHI fragment of the resulting pGEM-239-GP36 plasmid was transferred to pAcYM1, and a recombinant virus expressing the full length Gag precursor Gag p56 was selected as described below. A recombinant baculovirus expressing the bovine protease furin (Vey at al., 1994) under the control of the polyhedrin promoter was obtained by cloning furin into the SmaI site of the plasmid pVL 1392.

Example 3

Recombinant AcMNPV Expressing Viral Genes

Sf9 cells were transfected as described by O'Reilly et al. (1992) with a mixture of linearized AcNPV DNA (Invitrogen, San Diego, Calif.) and the baculovirus transfer vector DNA containing an SIV gene. The supernatant was harvested three days after transfection and recombinant virus plaques, which did not contain occlusion bodies, were selected by plaque assay. In each case 10–20 potential recombinant plaques were screened by PCR amplification, using a pair of primers corresponding to the flanking polyhedrin sequences (O'Reilly et al., 1992). The forward primer has the sequence 5'd(TTT ACT GTT TTC GTA ACA GTT TTG)3' (SEQ ID NO: 1) and the reverse primer sequence is 5'd(CAA CAA CGC ACA GAA TCT AGC)3' (SEQ ID NO:2). Briefly, plaque picks were scaled up by infection of Sf9 cells in 96 well plates. Wild type virus was used as a control. Cells were lysed by adding 200 µl of 0.5 N NaOH and neutralized with 40 µl of 5 M ammonium acetate for each well at two days post infection. 10 µl of 1:10 dilution of the lysate, and a control of 100 ng of recombinant transfer vector were used for PCR amplification. The size of PCR reaction products was determined on an agarose gel. Plaques that gave the same size fragment in the PCR reaction as the transfer vector, used for transfection, were subjected to three rounds of plaque purification. Expression of SIV specific proteins was confirmed by metabolic labeling and immunoprecipitation followed by SDS-polyacrylamide gel electrophoresis.

Example 4

Baculovirus infection, [$^{35}$S] radiolabeling, immunoprecipitation and SDS-PAGE Monolayers of Sf9 cells were infected with recombinant baculoviruses at a M.O.I. of 10. When a combination of two or three recombinants was used for coinfection, a M.O.I. of 10 was used for furin- and all Env-expressing recombinants, and a M.O.I. of 7 was used for the Pr56$^{gag}$-expressing recombinant AcNPV. After 1 h adsorption, the inoculum was replaced with SF900 II medium. At 18 to 24 h post infection, cells were radiolabeled with 100 µCi of [$^{35}$S] cysteine/methionine per ml of methionine-deficient Sf900 medium for 1 h and then chased for various times. For continuous labeling, 50 µCi of [$^{35}$S] per ml of a mixture of 75% met-deficient and 25% of complete medium were used. The medium was collected and cells were lysed in RIP buffer (150 mM NaCl; 50 mM Tris-HCl pH 7.5; 0.1% SDS; 1% Triton X100; 1% sodium deoxycholate; 1 mM EDTA). The samples were preclarified by centrifugation and immunoprecipitated overnight at 4° C. with 1 µl of SIV polyclonal antiserum from an infected rhesus macaque (provided by Dr. P. Marx) and 10 µl of protein A-agarose per 1 ml. The agarose beads were washed three times in RIP buffer, and proteins were characterized by SDS-polyacrylamide gel electrophoresis followed by autoradiography.

Example 5

Purification and Analysis of VLPs from Insect Cells

Sf9 cells were infected with recombinant baculoviruses at a M.O.I. of 10 for envelope expressing recombinants and at a M.O.I. of 7 for Gag-expressing recombinants. At two days post infection, the medium was harvested, centrifuged at low speed (1000 rpm, 20 min, Beckman GPR centrifuge) and VLPs were pelleted through a cushion of 20% sucrose in PBS at 120,000 g for 2 h. For large scale preparations VLPs were concentrated on the top of a 60% sucrose cushion, diluted and then loaded on a continuous 20–60% (wt/v) sucrose gradient. After centrifugation for 3 h at 39,000 rpm (Beckman SW 41 rotor), 1 ml fractions were collected and analyzed. Finally, particles were recovered by diluting corresponding fractions 1:3 with PBS and pelleting at 120,000 g for 1 h.

For Western blot analysis VLPs pellets were resuspended in SDS-PAGE loading buffer, proteins were separated on 8% polyacrylamide gels containing 0. 1% SDS, and then were electrophoretically transferred to nitrocellulose membranes (Bio-Rad, Melville, N.Y.). Membranes were probed with a 1:2000 dilution of anti-SIV polyclonal rhesus serum and with corresponding HRP-conjugated secondary antibodies. The bound anti-SIV antibodies were detected by a color reaction (Sambrook et al., 1989, supra) or by enhanced chemiluminescence as directed by the manufacturer (Amersham, Arlington Heights, Ill.).

Example 6

Biotinylation of Cell Surface Proteins

Sf9 cells were infected as described above. At 17–25 h post infection, cells were biotinylated by a procedure similar to that described by Lisanti et al. (1988). Briefly, monolayers of cells were washed three times with ice-cold PBS (pH 8.0) and treated with 0.5 mg/ml of sulfo-NHS-biotin (Pierce, Rockford, Ill.) in PBS for 30 min. on ice. To quench the reaction, cells were incubated with Sf900 II media supplemented with 10% fetal bovine serum for 10 minutes on ice, then washed 3 times in PBS containing 20 mM glycine and lysed in RIP buffer. After immunoprecipitation with anti-SIV antibodies, SDS-PAGE and Western blot, biotinylated proteins transferred to the nitrocellulose were probed with a 1:2,500 dilution of horseradish peroxidase-conjugated streptavidin (Fisher, Atlanta, Ga.) and detected by enhanced chemiluminescence.

Example 7

Electron Microscopy

At 30 h post infection cells were fixed with buffered 1% glutaraldehyde for 30 min. The cells were postfixed for 1 h with 1% osmium tetroxide, dehydrated with a graded ethanol series, and embedded for electron microscopy in (EM) bed 812 (Electron Microscopy Services, Ft. Washington, Pa.). Thin sections were prepared on a Reichert ultramicrotome, mounted on 300 mesh copper grids, stained with uranyl acetate and lead citrate, and examined with a Phillips CM10 electron microscope.

Example 8

Production of HIV VLPs

HIV-1 proviral clone pSG3.1 is available from the AIDS RRRP as catalog number 2003. The nucleotide sequence is available from Genbank via Accession #L02317. The pertinent literature reference is Ghosh et al., 1993.

To express the HIV-1 Gag precursor under the control of the late/very late Cap/Polh promoter, a 1718 bp BssHII-BclI fragment is excised from the proviral DNA, treated with Klenow polymerase to produce blunt ends, and the resultant fragment is cloned into the pAcYM1 vector. Alternatively, a 2716 bp BssHII-ClaI fragment is treated with Bal31 exonuclease to shorten the distance between the promoter and the ATG translation start codon from about 80 bp to about 47 bp, as in the SIV clone, then it is treated with Klenow polymerase to make the ends blunt, and the resulting DNA molecule is subcloned into pGEM11Z. After sequence analysis an EcoRI-BclI fragment is then ligated into pAcYM1.

The Env region of HIV-1 is subcloned as a Pacd-SphI fragment of 2660 bp. This encodes the full-length Env protein, but it does not include the open reading frames for the Tat and Rev proteins. There are 40 bp upstream of the Env translation initiation codon. The ends of that fragment are filled in with Klenow polymerase, and it is then ligated into the SmaI site of pc/pS1 or the BamHI site of pAcYM1.

The truncation of the SIVmac239 env coding sequence is obtained by site-directed oligonucleotide mutagenesis of C to T at position 8336, changing a CAG codon (which encodes Gln) to a TAG stop codon. This mutant gene produces a truncated form of the envelope protein.

Recombinant baculovirus expressing the Gag and full-length or truncated HIV-1 Env proteins are isolated by using the above plasmids according to the same general protocol as described for SIV derivatives hereinabove in Example 3. To produce VLPs carrying HIV-1 antigens, insect cells are coinfected with the present baculovirus vectors together with furin-expressing baculoviruses also as described hereinabove.

REFERENCES

Ball, J. M., Payne, S. L., Issel, C. J. and Montelaro, R. C. (1988). EIAV genomic organization: further characterization by sequencing of purified glycoproteins and cDNA. *Virology* 165, 601–5.

Boomer, S., Gasper, P., Whalen, L. R. and Overbaugh, J. (1994). Isolation of a novel subgroup B feline leukemia virus from a cat infected with FeLV-A. *Virology* 204, 805–810.

Chazal, N., Gay, B., Carriere, C., Tournier, J., and Boulanger, P. (1995). Human immunodeficiency virus type 1 MA deletion mutants expressed in baculovirus-infected cells: cis and trans effects on the Gag precursor assembly pathway. *J. Virol.* 69, 365–375.

Chen, P., Liu, Z. Q. and Wood, C. (1994). Use of TrpE fusion protein to identify antigenic domains within the BIV envelope protein. *J. Virol. Methods* 47, 331–343.

Cunningham, T. P., Montelaro, R. C. and Rushlow, K. E. (1993). lentivirus envelope sequences and proviral genomes are stabilized in Escherichia coli when cloned in low-copy-number plasmid vectors. *Gene* 124, 93–8.

Delchambre, M., Gheysen, D., Thines, D., Thiriart, C., Jacobs, E., Verdin, E., Horth, M., Burny, A. and Bex, F. (1989). The Gag precursor of simian immunodeficiency virus assembles into virus-like particles. *EMBO J.* 8, 2653–2660.

Dertzbaugh, M. T. and Elson, C. O., (1993). Comparative effectiveness of the cholera toxin B subunit and alkaline phosphatase as carriers for oral vaccines. *Infect. Immun.* 61, 48–55.

Dong, J., and Hunter, E. (1993). Analysis of retroviral assembly using a vaccinia/T7-polymerase complementation system. *Virology* 194, 192–199.

Dorfman, T., Mammano, F., Haseltine, W. A., and Gottlinger, H. G. (1994). Role of the matrix protein in the virion association of the human immunodeficiency virus type 1 envelope glycoprotein. *J. Virol.* 68, 1689–1696.

Eldridge, J. H. et al. (1989). Vaccine delivery system for oral immunization. *Curr. Top. Microbiol. Immunol.* 146, 59–66.

Elson, C. O. et al. (1984). A lavage technique allowing repeated measurement of IgA antibody in mouse intestinal secretions. *J. Immunol. Meth.* 67, 101–108.

Gabuzda, D. H., Lever, A., Terwilliger, E., Sodroski J. (1992). Effects of deletions in the cytoplasmic domain on biological functions of human immunodeficiency virus type 1 envelope glycoproteins. *Journal of Virology* 66, 3306–3315.

Ghosh, S. K., Fultz, P. N., Keddie, E., Saag, M. S., Sharp, P. M., Hahn, B. H. and Shaw, G. M. (1993). A molecular clone of HIV-1 tropic and cytopathic for human and chimpanzee lymphocytes. *Virology* 194, 858–864.

Guo, H. -G., Veronese, F., Tschachler, E., Pal, R., Kalyanaraman, V. S., Gallo, R. C., and Reitz, M. S., Jr. (1990). Characterization of an HIV-1 point mutant blocked in envelope glycoprotein cleavage. *Virology* 174, 217–224.

Haffar, O., Garrigues, J., Travis, B., Moran, P., Zarling, J., and Hu, S. -L. (1990). Human immunodeficiency virus-like, non-replicating Gag-Env particles assemble in a recombinant vaccinia virus expression system. *J. Virol.* 64, 2653–2659.

Haffar, O. K., Smithgal, M. D., Moran, P., Travis, B., Zarling, J., and Hu, S. -L. (1991). HIV-specific humoral and cellular immunity in rabbits vaccinated with recombinant human immunodeficiency virus-like Gag-Env particles. *Virology* 183, 487–495.

Haffar, O. K., Moran, P., Smithgal, M. D., Diegel, M. L., Sridhar, P., Ledbetter, J. A., Zarling, J., and Hu, S. -L. (1992). Inhibition of virus production in peripheral blood mononuclear cells from human immunodeficiency virus (HIV) type 1-seropositive donors by treatment with recombinant HIV-like particles. *J. Virol.* 66, 4279–4287.

Haigwood, N. L., Nara, P. L., Brooks. E., Van Nest, G. A., Ott, G., Higgins, K. W., Dunlop, N., Scandella, C. J., Eichberg J. W., and Steimer, K. S. (1992). Native but not denatured recombinant Human Immunodeficiency Virus type 1 gp120 generates broad-spectrum neutralizing antibodies in baboons. *J. Virol.* 66, 172–182.

Hallenberger, S., Bosch, V., Angliker, H., Shaw, E., Klenk, H. -D., & Garten, W. (1992). Inhibition of furin-mediated cleavage activation of HIV-1 glycoprotein gp160. *Nature* 360, 358–361.

Haynes, J. R., Cao, S. X., Rovinski, B., Sia, C., James, O., Decaban, G. A., and Klein, M. H. (1991). Production of immunogenic HIV-1 virus-like particles in stably engineered monkey cell lines. *AIDS Res. Hum. Retr.* 7, 17–27.

Hirsch, V. M., Edmondson, P., Murphy-Corb, M., Arbeille, B., Johnson, P. R., and Mullins, J. L. (1989). SIV adaptation to human cells. *Nature* (*London*) 341, 573–574.

Hu, S. -L., Kosowski, S. G., and Schaaf, K. F. (1987). Expression of envelope glycoproteins of human immunodeficiency virus by an insect virus vector. *J. Virol.* 176, 3617–3620.

Hughes, B. P., Booth, T. F., Belyaev, A. S., McIlroy, D., Owett, J., and Roy, P. (1993). Morphogenic capabilities of human immunodeficiency virus type 1 Gag and Gag-Pol proteins in insect cells. *Virology* 193, 242–255.

Jarvis, D. L., Fleming, J. -A. G. W., Kovacs, G. R., Summers, M. D., and Guarino, L. A. (1990). Use of early baculovirus promoters for continuous expression and efficient processing of foreign gene products in stably transformed lepidopteran cells. *Biotechnology* 8, 950–955.

Jenkins, S., Grits, L., Fedor, C. H., O'Neill, E. M.,Cohen, L. K., and Panicali, D. L. (1991). Formation of lentivirus particles by mammalian cells infected with recombinant fowlpox virus. *AIDS Res. Hum. Retr.* 7, 991–998.

Julius, D. et al. (1984). Isolation of the putative structural gene for the lysine-arginine-cleaving endopeptidase required for processing of yeast pre-pro-alpha factor. *Cell* 37, 1075–1089.

Krausslich, H. -G., Ochsenbauer, C., Traenckner, A. -M., Mergener, K., Facke, M., Gelderblom, H. R., and Bosch, V. (1993). Analysis of protein expression and virus-like particle formation in mammalian cell lines stably expressing HIV-1 gag and env gene products with or without active HIV proteinase. *Virology* 192, 605–617.

Kuroda, K., Hauser, C., Rott, R., Klenk, H. -D., and Doerfler, W. (1986). Expression of the influenza virus haemagglutinin in insect cells by a baculovirus vector. *EMBO J.* 5, 1359–1365.

Lee, P. P., and Linial, M. L. (1994). Efficient particle formation can occur if the matrix domain of human immunodeficiency virus type 1 Gag is substituted by a myristilation signal. *J. Virol.* 68, 6644–6654.

Lehner, T. et al. (1992). Induction of mucosal and systemic immunity to a recombinant simian immunodeficiency viral protein. *Science* 258, 1365–1369. Lisanti, M. P., Sargiacomo, M., Graeve, L., Saltiel, A. R., and Rodriguez-Boulan, E. (1988). Polarized apical distribution of glycosyl-phosphatidylinositol-anchored proteins in a renal epithelial cell line. *Proc. Natl. Acad. Sci. USA* 85, 9557–9561.

Luo, L., Li, Y., and Kang, C. Y. (1990). Expression of Gag precursor protein and secretion of virus-like Gag particles of HIV-2 from recombinant baculovirus-infected insect cells. *Virology* 179, 874–880.

Marx, P. A., et al. 1993). Protection against SIV Vaginal transmission with microencapsulated vaccine. *Science.* 260, 1323–1327.

McCune, J. M., Rabin, L. B., Feinberg, M. B., Leiberman, M., Kosek, J. C., Reyes, G. R., and Weissman, I. L. (1988). Endoproteolytic cleavage of gp160 is required for the activation of human immunodeficiency virus. *Cell* 53, 55–67.

Moldoveanu, Z. et al. (1993) Oral immunization with influenza virus in biodegradable microspheres. *J. Inf. Dis.* 167, 84–90.

Moldoveanu, Z. et al. (1989). Immune responses to influenza virus in orally and systemically immunized mice. *Curr. Top. Microbiol. Immunol.* 146, 91–99.

Moore, J., Lewis, G. K., and Robinson, J. (1993). Which gp160 vaccine? *Nature* 361, 503.

Morikawa, S., Booth, T. F., and Bishop, D. H. L. (1991). Analyses of the requirements for the synthesis of virus-like particles by feline immunodeficiency virus Gag using baculovirus Oroszlan, S., Copeland, T. D., Rice, N. R., Smythers, G. W., Tsai, W. P., Yoshinaka, Y. and Shimotohno, K. (1984). Structural and antigenic characterization of the proteins in human T-cell leukemia viruses and their relationships to the gene products of other retroviruses. *Princess Takamatsu Symp.* 15, 147–157. vectors. *Virology* 183, 288–297.

Morikawa, Y., Barsov, E., and Jones, I. (1993). Legitimate and illegitimate cleavage of human immunodeficiency virus glycoproteins by furin. *J. Virol.* 67, 3601–3604.

Mulligan, M. J., Yamshchikov, G. V., Ritter, G. D., Gao, F., Jin, M. J., Nail, C. D., Spies, C. P., Hann, B. H., and Compans, R. W. (1992). Cytoplasmic domain truncation enhances fusion activity by the exterior glycoprotein complex of human immunodeficiency virus type 2 in selected cell types. *J. Virol.* 66, 3971–3975.

O'Reilly, D. R., Miller, L. K., and Luckov, V. A. (1992). Baculovirus expression vectors: a laboratory manual. W. H. Freeman and Company, New York.

Oroszlan, S., Copeland, T. D., Rice, N. R., Smythers, G. W., Tsai, W. P., Yoshinaka, Y. and Shimotohno, K. (1984). Structural and antigenic characterization of the proteins in human T-cell leukemia viruses and their relationships to the gene products of other retroviruses. *Princess Takamatsu Symp.* 15, 147–157.

Overton, H. A., Fujii, Y., Price, I. R., and Jones, I. M. (1989). The protease and gag gene products of the human immunodeficiency virus: authentic cleavage and post-translational modification in an insect cell expression system. *Virology* 170, 107–116.

Page, K. A., Stearns, S. M., and Littman, D. R. (1992). Analysis of mutations in the V3 domain of gp160 that affect fusion and infectivity. *J. Virol.* 66, 524–533.

Pancino, G., Castelot, S. and Sonigo, P. (1995). Differences in feline immunodeficiency virus host cell range correlate with envelope fusogenic properties. *Virology* 206, 796–806.

Pique, C., Tursz, T. and Dokhelar, M. C. (1990). Mutations introduced along the HTLV-I envelope gene result in a non-functional protein: a basis for envelope conservation? *EMBO J.* 9, 4243–4248.

Ray, R. et al. (1993). Microencapsulated human parainfluenza virus produces a protective immune response. *J. Inf. Dis.* 167, 752–755. Ritter, D. G., Mulligan, M. J., Lydy, S. L., and Compans, R. W. (1993). Cell fusion activity of the simian immunodeficiency virus envelope protein is modulated by the intracytoplasmic domain. *Virology* 197, 255–264. Rohn, J. L., Linenberger, M. L., Hoover, E. A. and Overbaugh J. (1994). Evolution of feline leukemia virus variant genomes with insertions, deletions, and defective envelope genes in infected cats with tumors. *J Virol.* 68, 2458–2467.

Rovinski, B., Haynes, J. R., Cao, S. X., James, O., Sia, C., Zolla-Pazner, S., Matthews, T. J., and Klein, M. H. (1992). Expression and characterization of genetically engineered Human Immunodeficiency Virus-like particles containing modified envelope glycoproteins: implications for development of cross-protective AIDS vaccine. *J. Virol.* 66, 4003–4012.

Royer, M., Cerutti, M., Gay, B., Hong, S. -S., Devauchelle, G., and Boulanger, P. (1991). Functional domains of HIV-1 Gag polyprotein expressed in baculovirus-infected cells. *Virology* 184, 417–422.

Rusche, J. R., Lynn, D. L., Robert-Guroff, M., Langlois, A. J., Lyerly, H. K., Carson, H., Krohn, K., Ranki, A., Gallo, R. C., Bolognesi, D. P., Putney, S. S., and Matthews, T. J. (1987). Humoral immune response to the entire human immunodeficiency virus envelope glycoprotein made in insect cells. *Proc. Natl. Acad. Sci. USA* 84, 6924–6928.

Rushlow, K., Olsen, K., Stiegler, G., Payne, S. L., Montelaro, R. C. and Issel, C. J. (1986). Lentivirus genomic organization: the complete nucleotide sequence of the env gene region of equine infectious anemia virus. *Virology* 155, 309–321.

Sagata, N. and Ikawa, Y. (1984). BLV and HTLV-I: their unique genomic structures and evolutionary relationship. *Princess Takamatsu Symp.* 15, 229–240.

Schiltz, R. L., Shih, D. S., Rasty, S., Montelaro, R. C. and Rushlow, K. E. (1992). Equine infectious anemia virus gene expression: characterization of the RNA splicing pattern and the protein products encoded by open reading frames S1 and S2. *J Virol.* 66, 3455–65.

Spies, C. P., Ritter, G. D., Jr., Mulligan, M. J., & Compans, R. W. (1994). Truncation of the cytoplasmic domain of the simian immunodeficiency virus envelope glycoprotein alters conformation of the external domain. *J. Virol.,* 68, 585–591.

Thiem, S. M. and Miller, L. K. (1990). Differential gene expression mediated by late, very late and hybrid baculovirus promoters. *Gene* 91, 87–94.

Vey, M., Schafer, W., Berghofer, S., Klenk, H -D., and Garten, W. (1994). Maturation of the trans-Golgi network protease furin: compartmentalization of propeptide removal, substrate cleavage, and COOH-terminal truncation. *J. Cell Biol.,* 127, 1 829–1842.

Vile, R. G., Schulz, T. F., Danos, 0. F., Collins, M. K. and Weiss, R. A. (1991). A murine cell line producing HTLV-I pseudotype virions carrying a selectable marker gene. *Virology* 180, 420–424.

Vzorov, A. N., Bukrinsky, M. I., Grigoriev, V. B., Tentsov, Y. Y., and Bukrinskaya, A. G. (1991). Highly immunogenic human immunodeficiency virus-like particles are produced by recombinant vaccinia virus-infected cells. *AIDS Res. Hum. Retr.* 7, 29–36.

Wang, B., Agadjanyan, M. G., Srikantan, V., Ugen, K. E., Hall, W., Kaplan, M. H., Dang, K., Williams, W. V. and Weiner, D. B. (1993). Molecular cloning, expression, and biological characterization of an HTLV-II envelope glycoprotein: HIV-1 expression is permissive for HTLV-II-induced cell fusion. *AIDS Res. Hum. Retroviruses* 9, 849–60.

Wang, C. -T., Zhang, Y., McDermott, J., and Barklis, E. (1993). Conditional infectivity of a human immunodeficiency virus matrix domain deletion mutant. *J. Virol.* 67, 7067–7076.

Wells, D. E., and Compans, R. W. (1990). Expression and characterization of a functional human immunodeficiency virus envelope glycoprotein in insect cells. *Virology* 176, 575–586. Willey, R. L., Bonifacino, J. S., Potts, B. J., Martin, M. A., and Klausner, R. D. (1988). Biosynthesis, cleavage, and degradation of the human immunodeficiency virus 1 envelope glycoprotein gp160. *Proc. Natl. Acad. Sci. USA* 85, 9580–9584.

Wills, J. W., and Craven, R. C. (1991). Form, function, and use of retroviral Gag proteins. *AIDS* 5, 639–654.

Yu, X., Yuan, X., Matsuda, Z., Lee, T. -H. and Essex, M. (1992). The matrix protein of human immunodeficiency virus type 1 is required for incorporation of viral envelope protein into mature virus. *J. Virol.* 66, 4966–4971.

Yuan, X., Yu, X., Lee, T. -H., and Essex, M. (1993). Mutations in the N-terminal region of human immunodeficiency virus type 1 matrix protein block intracellular transport of the Gag precursor. *J. Virol.* 67, 6387–6394.

Zingler, K., and Littman, D. R. (1993). Truncation of the cytoplasmic domain of the simian immunodeficiency virus envelope glycoprotein increases Env incorporation into particles and fusogenicity and infectivity. *J. Virol.* 67, 2824–2831.

Zhou, W., Parent, L. J., Wills, J. W., and Resh, M. D. (1994). Identification of membrane-binding domain within the amino-terminal region of human immunodeficiency virus type 1 Gag protein which interacts with acidic phospholipids. *J. Virol.* 68, 2556–2569.

We claim:

1. A method of making a retrovirus-like particle, said method comprising the steps of:
    (a) operably linking a coding sequence for a truncated envelope protein of a retrovirus to a baculovirus early promoter, late promoter, or hybrid late/very late promoter, and inserting into baculovirus vector to form an envelope protein expression construct;
    (b) operably linking a protease-encoding sequence to regulatory sequences in a vector for expression in insect cells to form a protease expression construct;
    (c) simultaneously introducing into an insect cell the envelope protein expression construct of step (a) and the protease expression construct of step (b) and allowing for expression of the truncated retrovirus envelope protein and the protease,
    whereby retrovirus-like particles are formed by the insect cells of step (c).

2. The method of claim 1, wherein the protease is furin.

3. The method of claim 1, wherein the retrovirus-like particles are a Simian Immunodeficiency Virus-like particle, a Human Immunodeficiency Virus-like particle, a bovine immunodeficiency virus-like particle, a bovine leukemia virus-like particle, a feline leukemia virus-like particle, a feline immunodeficiency virus-like particle, an equine infectious anemia virus-like particle and a human T cell leukemia virus type I virus-like particle.

4. The method of claim 1, wherein the truncated retrovirus envelope protein lacks from about 5% to about 90% of its cytoplasmic domain.

5. The method of claim 1, wherein the hybrid late/very late promoter is an *Autographa Californica* nuclear polyhedrosis virus Cap/Polh promoter.

6. A retrovirus-like particle made by the method of claim 1.

7. An immunogenic composition comprising the retrovirus-like particle of claim 6 and a pharmacologically acceptable carrier.

8. The immunogenic composition of claim 7, wherein said retrovirus-like particle comprises a truncated retrovirus envelope protein, wherein the truncated envelope protein retains antigenic determinants of a corresponding full-length envelope protein.

9. The immunogenic composition of claim 8, wherein the truncated retrovirus envelope protein lacks from about 5% to about 90% of its cytoplasmic domain.

10. The immunogenic composition of claim 7, wherein said the retrovirus-like particle is a Simian Immunodeficiency Virus-like particle, a Human Immunodeficiency Virus-like particle, a bovine immunodeficiency virus-like particle, a bovine leukemia virus-like particle, a feline leukemia virus-like particle, a feline immunodeficiency virus-like particle, an equine infectious anemia virus-like particle and a human T cell leukemia virus type I virus-like particle.

11. The immunogenic composition of claim 7 further comprising an immunological adjuvant.

12. A method of generating an immunological response in an animal, said method comprising the step of administering the immunogenic composition of claim 7 to said animal.

13. The method of claim 12, wherein said retrovirus-like particle is a bovine immunodeficiency virus-like particle, a bovine leukemia virus-like particle, a feline leukemia virus-like particle, a feline immunodeficiency virus-like particle, an equine infectious anemia virus-like particle and a human T cell leukemia virus type I virus-like particle.

14. The method of claim 12, wherein said retrovirus-like particle is a Simian Immunodeficiency Virus-like particle or a Human Immunodeficiency Virus-like particle.

15. The method of claim 12, wherein administration is oral.

16. The method of claim 12, wherein the step of administering the immunological composition is administered to a mucosal surface.

17. The method of claim 16, wherein said mucosal surface is an intranasal surface.

18. The method of claim 16, wherein said mucosal surface is a vaginal surface.

19. The method of claim 16, wherein said mucosal surface is a rectal surface.

20. The method of claim 16, wherein said mucosal surface is a gastric surface.

21. A method of determining exposure of an animal or human to a retrovirus, said method comprising the steps of:
    (a) contacting a biological fluid of said animal or human with the retrovirus-like particle of claim 6, wherein said retrovirus-like particle is of the same retrovirus type to which exposure is being determined, under conditions which are permissive for binding of antibodies in said biological fluid with said retrovirus-like particles; and
    (b) detecting binding of antibodies within the biological fluid with the retrovirus-like particles in step (a),
    whereby exposure of said animal or human to said retrovirus is determined by the detection of antibodies bound to said retrovirus-like particles in step (b).

22. The method of claim 21, wherein the step of detecting is by use of a labeled second antibody which is specific to antibodies in the biological fluid being tested in step (a).

23. The method of claim 21, wherein said biological fluid is blood, semen, seminal fluid serum, saliva, a vaginal secretion, or an intestinal secretion.

24. The method of claim 21 wherein said second antibody is specific for IgA.

* * * * *

UNITED STATES PATENT AND TRADEMARK OFFICE
CERTIFICATE OF CORRECTION

PATENT NO. : 6,077,662
DATED : June 20, 2000
INVENTOR(S) : Compans et al.

It is certified that error appears in the above-indentified patent and that said Letters Patent is hereby corrected as shown below:

In column 4, line 49, please delete "Vane" and replace with --Lane--.

In column 6, line 7, please delete "Pr56mn" and replace with --Pr56$^{gag}$--.

In column 7, line 10, please insert a comma between "cells" and "the".

In column 10, line 65, please delete "abou" and replace with --about--.

In column 17, line 16, please delete "Pacd-SphI" and replace with --PacI-SphI-.

In column 19, line 29, please begin a new paragraph with "Lisanti, M.P.".

UNITED STATES PATENT AND TRADEMARK OFFICE
CERTIFICATE OF CORRECTION

PATENT NO. : 6,077,662
DATED : June 20, 2000
INVENTOR(S) : Compans et al

It is certified that error appears in the above-indentified patent and that said Letters Patent is hereby corrected as shown below:

In column 19, lines 55-64 please move the line "vectors. *Virology* 183:288-297.)" to line 56 after the word "baculovirus" and begin a new paragraph with "Oroszlan, S.".

In column 20, line 34, please begin a new paragraph with "Ritter, D.G.".

In column 20, line 38, please begin a new paragraph with "Rohn, J.L.".

In column 22, line 9, please begin a new paragraph with "Willey, R.L.".

In column 23, claim 1, last line, please insert --wherein the insect cell simultaneously expresses a retrovirus Gag protein,-- following "protease,".

In column 23, claim 8, line 2, please insert --retrovirus Gag protein and a-- between "a" and "truncated".

Signed and Sealed this

Seventeenth Day of April, 2001

Attest:

NICHOLAS P. GODICI

*Attesting Officer*   *Acting Director of the United States Patent and Trademark Office*

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 24 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "Oligonucleotide."

(iii) HYPOTHETICAL: NO (xi) SEQUENCE DESCRIPTION: SEQ ID NO:1:

TTTACTGTTT TCGTAACAGT TTTG      24

(2) INFORMATION FOR SEQ ID NO:2:

(i) SEQUENCE CHARACTERISTICS:
      (A) LENGTH: 21 base pairs
      (B) TYPE: nucleic acid
      (C) STRANDEDNESS: single
      (D) TOPOLOGY: linear (ii) MOLECULE TYPE: other nucleic acid

```
        (A) DESCRIPTION: /desc = "Oligonucleotide."

(iii) HYPOTHETICAL: NO (xi) SEQUENCE DESCRIPTION: SEQ ID NO:2:

CAACAACGCA CAGAATCTAG C                                                  21
```